United States Patent
Jacobson et al.

(10) Patent No.: US 7,425,319 B2
(45) Date of Patent: *Sep. 16, 2008

(54) METHOD FOR ENHANCING PROTECTIVE CELLULAR RESPONSES TO GENOTOXIC STRESS IN SKIN

(75) Inventors: Elaine L. Jacobson, Lexington, KY (US); Myron K. Jacobson, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 242 days.

This patent is subject to a terminal disclaimer.

(21) Appl. No.: 10/256,403

(22) Filed: Sep. 27, 2002

(65) Prior Publication Data

US 2004/0147491 A1    Jul. 29, 2004

Related U.S. Application Data

(62) Division of application No. 09/765,129, filed on Jan. 18, 2001, now Pat. No. 6,552,050, which is a division of application No. 09/452,617, filed on Dec. 1, 1999, now Pat. No. 6,337,065.

(60) Provisional application No. 60/110,482, filed on Dec. 1, 1998.

(51) Int. Cl.
*A61K 7/42* (2006.01)
*A61K 7/00* (2006.01)
*A61K 31/44* (2006.01)

(52) U.S. Cl. .......... 424/59; 424/401; 514/351; 514/353; 514/356

(58) Field of Classification Search .......... 424/401, 424/400; 514/356, 351, 353
See application file for complete search history.

(56) References Cited

U.S. PATENT DOCUMENTS

| | | | |
|---|---|---|---|
| 4,683,310 A | 7/1987 | Dalton et al. | |
| 4,775,763 A | 10/1988 | Dalton et al. | |
| 4,847,260 A * | 7/1989 | Abe et al. | 514/279 |
| 5,939,082 A * | 8/1999 | Oblong et al. | 424/401 |

* cited by examiner

*Primary Examiner*—Sreeni Padmanabhan
*Assistant Examiner*—Layla Soroush
(74) *Attorney, Agent, or Firm*—Fulbright & Jaworski LLP

(57) ABSTRACT

The present invention is directed to methods of using pro-NAD agents capable of enhancing the dermal and epidermal skin cell NAD content. These pro-NAD agents may be administered topically, orally, or parenterally to enhance DNA repair and other protective responses to DNA damage. The invention further relates to pharmaceutical compositions comprising pro-NAD agents that effectively elevate intracellular NAD content. Finally, the invention relates to the method of using the pro-NAD agents to treat disorders such as sunburn and other skin deterioration that results from DNA damage in skin cells.

12 Claims, 16 Drawing Sheets

Human Skin Cells in Sub-Optimal Niacin Decreased NAD Content
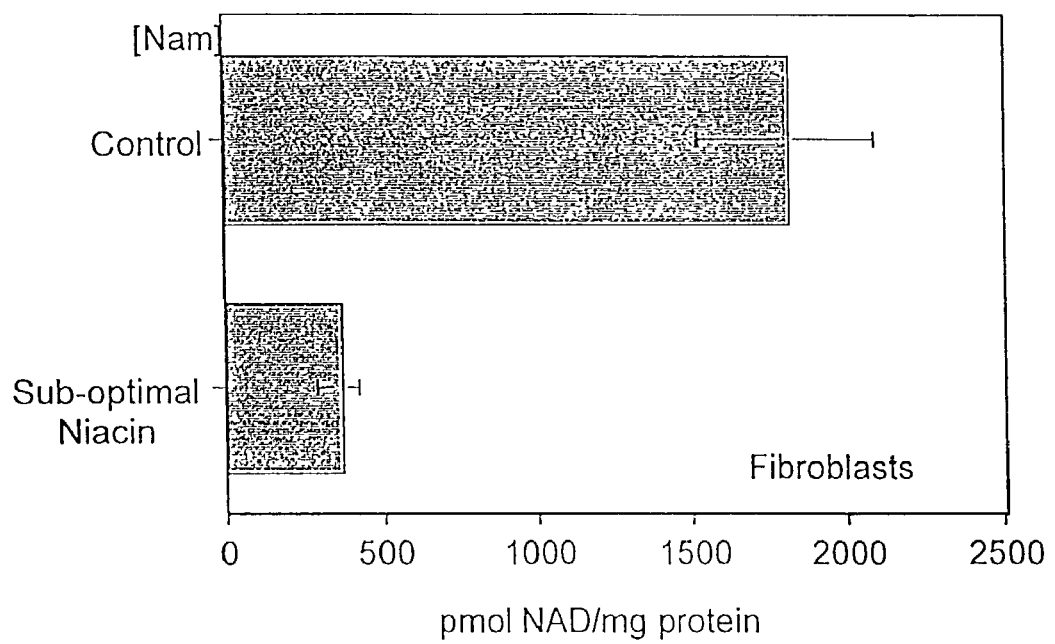
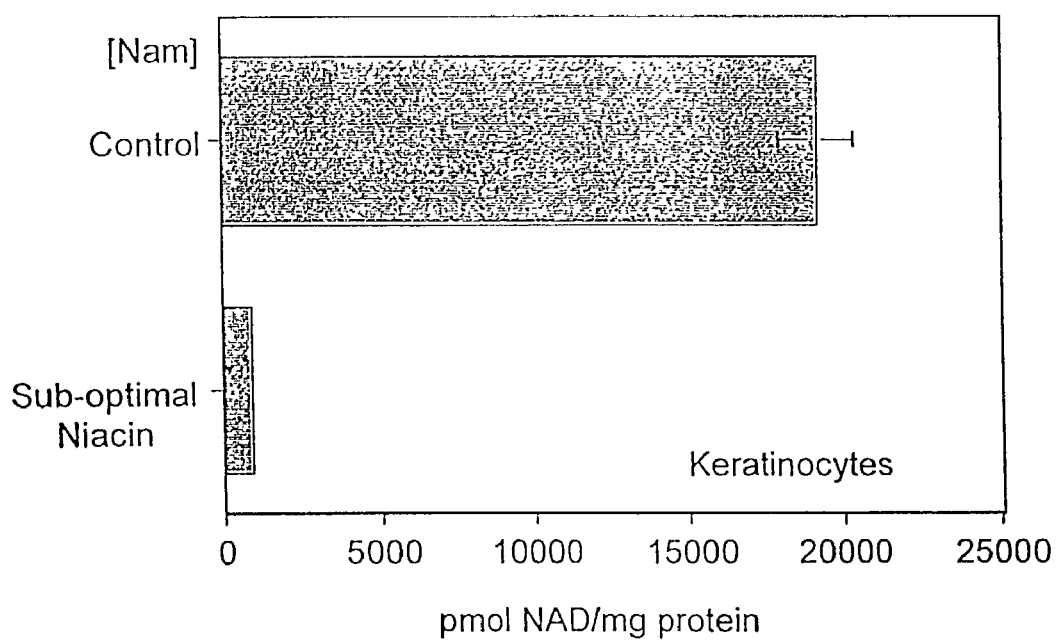
Figure 4

WESTERN BLOT ANALYSIS OF P53 IN CELL EXTRACTS
FROM CELLS WITH DECREASED NAD CONTENT
*FIG. 9A*
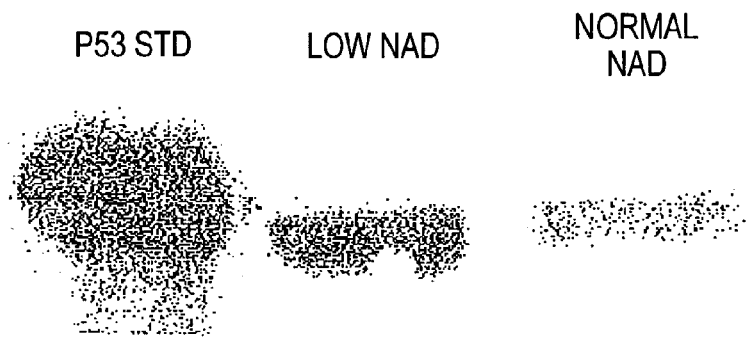
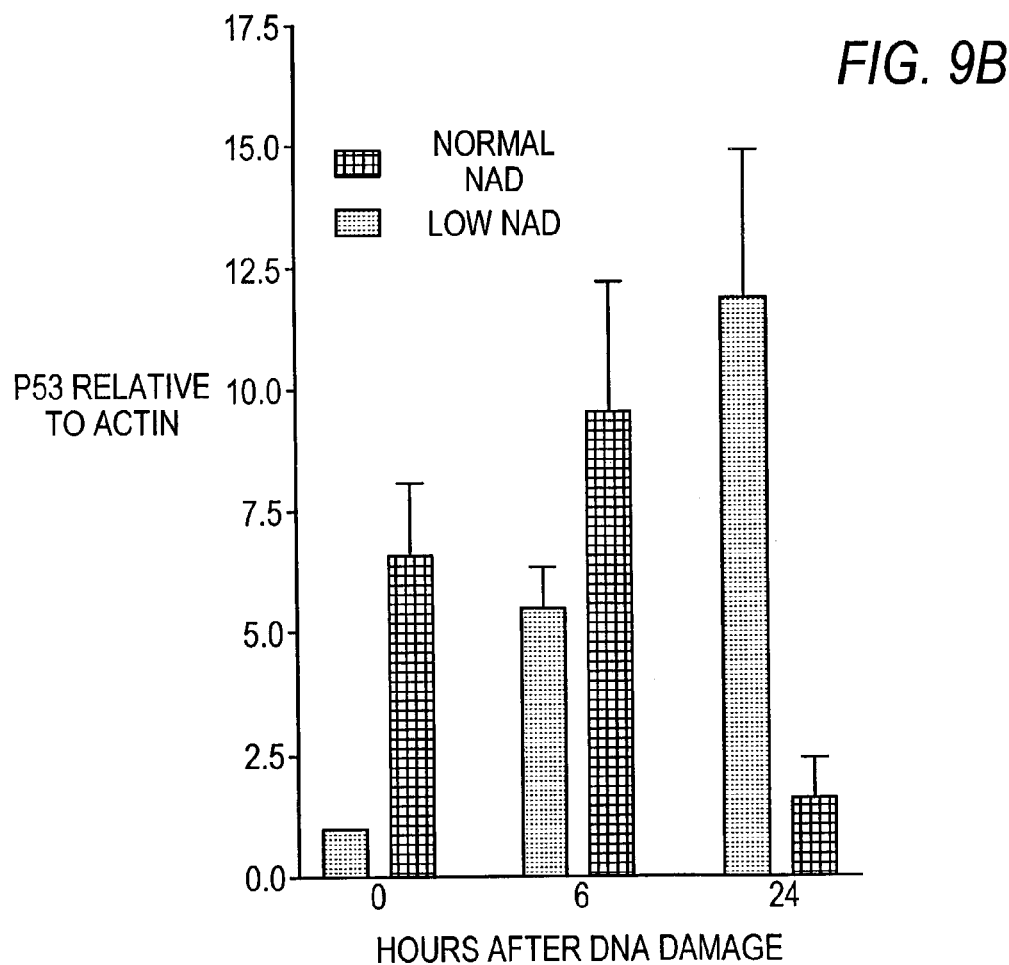
*FIG. 9B*

ASSESSMENT OF DNA INTEGRITY IN HUMAN EPITHELIAL CELLS BY COMET ASSAY

METHOD FOR ENHANCING PROTECTIVE CELLULAR RESPONSES TO GENOTOXIC STRESS IN SKIN

CROSS REFERENCE TO RELATED APPLICATIONS

This application is a divisional of application Ser. No. 09/765,129, filed Jan. 18, 2001, now U.S. Pat. No. 6,552,050, which is a divisional of application Ser. No. 09/452,617, filed Dec. 1, 1999, now U.S. Pat. No. 6,337,065. This application claims benefit of provisional patent application Ser. No. 60/110,482 filed Dec. 1, 1998. The entire disclosure of provisional patent application Ser. No. 60/110,482 is hereby incorporated by reference.

BACKGROUND

1. Field of the Invention

The invention is directed to methods and composition of using organic molecules termed pro-NAD agents capable of enhancing dermal and epidermal skin cell NAD content with a resulting enhancement of DNA repair and other protective responses to genotoxic stress in skin.

2. Description of the Background

The present application relates to methods and compositions capable of modulating and upregulating the cellular nicotinamide-adenine-dinucleotide (NAD) content by the topical application of chemical agents for the purpose of enhancing natural protective responses of skin cells to DNA damage. The methods and compositions are effective for the prevention and treatment of skin deterioration that results from DNA damage to cells of the skin. The symptoms of such skin deterioration are many and typically include the loss of moisture, fine lines, deep lines, wrinkles, and loss of elasticity as well as atrophic sclerosis and other blemishes of skin. Skin deteriorates with age as a natural consequence of prolonged exposure to internal and external factors. Internal deterioration factors include natural metabolic byproducts such as free radicals which cause the aging of all tissues. External deterioration factors include ionizing radiation such as sunlight and chemical insults such as pollution and cigarette smoke. In theory, skin care methods and compositions should inhibit, or slow the process of skin deterioration by counteracting these internal and external factors. Unfortunately, current methods and compositions for skin care are generally reactive rather than proactive. That is, current methods and compositions reduce or obscure the signs of aging but have minimal or no effect on the underlying progressive and cumulative biochemical processes that cause skin deterioration. It is therefore desirable to have a skin care method and composition which not only reduce the symptoms of deterioration but also treat the underlying causes of skin deterioration in such a way that deterioration can actually be retarded. To understand the limitations of current methods and compositions, it is necessary to understand the function and structure of the skin and the mechanisms of skin deterioration.

At ten pounds, the skin is the largest organ in the body. FIG. 1 shows a diagram of skin marking the location of the two major cell types present in skin, namely fibroblasts located in the dermal layer of the skin and keratinocytes located in the epidermal layer of the skin. The skin provides the first line of defense between the body's interior and harmful environmental insults by well established physical and biochemical mechanisms. Physical protection mechanisms include the relatively impermeable barrier the skin provides. The skin can, to some extent, repel and absorb insults such as chemicals and ultraviolet light so that while the skin may be damaged, the underlying tissue is preserved. Biochemical mechanisms include the innate and acquired immune systems. Microbiological pathogens are repelled by immune responses at the epidermal level involving Langerhans cells, keratinocytes, cytokines, polynuclear cells, endothelial cells, mast cells, and lymphocytes.

Structurally, the skin comprises epithelial tissue (the epidermis) in the outer layer and beneath it, connective tissue (the dermis), and beneath that, the fatty tissue (hypodermis). The epidermis is not vascularized and regenerates every four to six weeks. Its primary function is to maintain the body's skin integrity, acting as a physical barrier to toxic agents, dirt, bacteria, microorganisms, and physical insults. The dermis is beneath the epidermis and functions by providing strength, support, blood, and oxygen to the skin. The principal cell components of the dermis are fibroblasts although it also contains sweat glands, sebaceous glands, hair follicles, and small fat cells. Hypodermis, also known as the superficial fascia, attaches the dermis to the underlaying structures. Its function is to promote an ongoing blood supply to the dermis for regeneration.

The mechanisms of skin deterioration involve a gradual and progressive process that beings from birth. Internal factors that contribute to skin aging include toxic metabolic byproducts, autoimmune diseases, and genetic predisposition. The consequences of internal deterioration can be observed over the entire body from the skin to the internal organs. While the mechanisms of internal deterioration are not completely understood, somatic mutation has been shown to be a contributing factor. Under the somatic mutation theory, cells gradually lose their youthful characteristics and their capacity to divide by the accumulation of mutations (errors) in their genetic code. These mutations may be caused by free radicals or alkylating agents generated in metabolism that lead to unrepaired DNA damage. Over time, mutations accumulate in the body until the cell can no longer divide or produce functional proteins.

External factors such as chemical and physical agents in the environment can also cause DNA damage that leads to skin deterioration. The external factors include sunlight, pollution, and ingested chemicals from smoking or from food.

Deterioration of skin leads to changes in dermal thickness and elasticity due to increased crosslinking of collagen. Epidermal regeneration increases in activity while metabolism, sweat glands, and vascularization, all decrease in activity. The damage from internal and external factors is progressive and cumulative and results in the appearance of deterioration associated with aged skin.

Related to the somatic mutation theory, both internal and external factors contribute to oxidative stress, which in turn results in DNA damage. In humans, oxidative stress and DNA damage is caused by factors such as hyperbaric oxygen, gamma radiation, ultraviolet radiation, ozone, peroxides, free radicals, alkylating agents, and redox cycling drugs. While total oxidative stress and DNA damage may be reduced by living in a low pollution environment and avoiding sunlight, they cannot be eliminated. Some factors like ionizing radiation are present in all environments at a low level and other factors are byproducts of metabolism and cannot be totally eliminated. Further, urban environments have high levels of ground level pollution from a variety of sources that are not likely to be reduced in the near future. However, while DNA damage cannot be avoided, not all DNA damage leads to mutations.

DNA damage does not necessarily lead to mutation because a normal cell contains diverse and effective systems for repairing damaged DNA. There are at least 50, and possibly more than 100 genes involved in DNA repair. The importance of good DNA repair in retarding skin deterioration is most noticeable in patients that suffer from DNA repair defects such as xeroderma pigmentosum (XP). XP have early and accelerated skin deterioration, clearly demonstrating the importance of DNA repair to reducing deterioration of the skin. In addition to DNA repair, a normal cell also has systems that invoke "programmed cell death" by a process termed apoptosis. The process of apoptosis effectively "erases" cells damaged beyond the point of repair. These natural defense mechanisms of the skin have been ignored by current methods of preventing skin deterioration.

Many creams, lotions, bath oils, ointments, pastes, cleansers, covers, and powders claim to be effective in preventing skin deterioration. However, all current methods and compositions have severe disadvantages in that they are limited in their ability to retard skin deterioration. Most over the counter skin care products soften deteriorated skin or otherwise reduce the symptoms of deteriorated skin with no effect on the underlying biochemical processes involved in deterioration. Many existing skin care products and cosmetics function by providing moisture to the skin, preventing moisture loss, or providing cover to obscure the visible signs of deterioration. While traditional cosmetics may have effects on appearance, these effects are evanescent and any apparent improvement disappears as soon as the product use is discontinued. Further, traditional cosmetics' effectiveness decrease upon exposure to moisture and thus cosmetics must be reapplied after exercise, swimming, or any other exposure to moisture. Some cosmetics contain metals (e.g., iron and copper) which may actually increase skin levels of free radical formation and possibly promote deterioration. As the use of such products does not prevent deterioration, more and more of the product is needed as time progresses to obscure the increasing severe condition of the underlying skin.

Another method for treating aging skin is the use of alpha hydroxy acids (AHA) such as lactic acid, citric acid, glycolic acid, malic acids; beta hydroxy acids (BHA) such as salicylic acid; and retinoids (e.g. tretinoin (retin A), retinol and retinal), as exfoliants. These agents help remove the uppermost layer of skin to expose the more youthful underlying skin. However, there is a danger that by removing the outer layer of skin, AHA, BHA and retinoids can compromise the important barrier function of skin. It is possible that the use of these exfoliants may accelerate skin aging by removing the protective outer layer of skin. Exfoliants and other ingredients may also increase the skin's sensitivity to environmental conditions such as sunlight, wind, cold temperature and dry air, or to chemical agents such as antigens, or may exacerbate the irritation attributable to a pre-existing skin disease. Another disadvantage of AHA, BHA and retinoids is that these compounds are potential skin irritants which can induce side effects such as sore, red skin.

Another popular method for skin treatment is the use of sunblocks. Sunblock (i.e., sunscreen) refers to any chemical that when applied to the skin, reduces the amount of UV light that reaches the skin. By preventing UV absorptions that cause genomic mutations, sunblocks can decrease and retard skin deterioration. Sunblocks were originally designed to prevent sunburn (also known as erythema), an acute reaction to overexposure to the sun. The strength of sunblocks is measured by the SPF index (Sun Protection Factor). An SPF value of 15, for example, will provide 15 times the protection of bare skin to sunburns. However, it should be noted that the SPF values, which measures resistance to sunburn, cannot be extrapolated to photoaging protection, which is caused by constant low level environmental insults. That is, a sunblock with an SPF factor of 15 will not reduce photoaging 15 fold. There is also a danger that chemicals in some sunblocks will increase DNA damage and contribute to skin deterioration. Finally, every major class of sunblock has been linked to skin allergies.

Finally, there are agents that are physical blends of existing agents. A physical blend is a mixture of two or more chemicals. Physical blends can be mixed powders, mixed solutions, mixed emulsions, mixed colloidal solutions, particles in solutions, and the like. An example of a physical blend may be a covering or coloring cosmetic mixed with a sunblock (titanium dioxide) and a hydroxy acid.

In summary, current methods of skin treatment are mostly reactive in that they treat the symptoms of deterioration after the damage is done. Current skin treatment methods do not reverse damage to the dermal tissue. There is a need for topical skin care products that are proactive rather than reactive. A proactive product is one that will assist the skin in resisting DNA damage by either preventing damage or assisting in repair of any damage.

SUMMARY OF THE INVENTION

The present invention overcomes many of the limitations, problems and disadvantages associated with current strategies and designs for preventing skin deterioration and provides methods and composition for the treatment of skin deterioration.

One object of the invention is directed to a method and composition for treating skin to prevent and slow the deterioration process.

It is another objective of the invention to provide a method to retard deterioration of the skin by enhancing the skin's natural DNA repair mechanism.

It is another object of the invention to provide a method for the sustained release of pro-NAD agents to skin cells.

Another object of the invention is directed to a composition for topical application comprising one or more pro-NAD agent that promote cellular DNA repair.

One embodiment of the invention is directed to a pharmaceutical composition for a subject in need of an elevation of intracellular NAD content. The pharmaceutical composition comprises a pro-NAD agent and a pharmaceutically acceptable carrier. The pro-NAD agent is present in the pharmaceutical composition at a concentration sufficient to elevate intracellular NAD in the subject. The pharmaceutical composition maybe adapted for topical administration to the skin. Adaptation may included the inclusion of a pharmaceutically acceptable carrier which is suitable for use in topical applications.

The pro-NAD agents of the invention may comprise one or more compounds with the following formula:

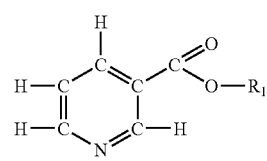

where $R_1$ is a hydrogen or any chemical group that can be enzymatically or chemically removed to generate nicotinic acid following administration to said subject. A chemical group is any chemical molecule such as, for example, any branched or unbranched (straight) alkane, alkene, or alkyne group. In a preferred embodiment, the chemical group is a group such as an ester, that can be removed by an esterase following the administration of the pharmaceutical composition to the subject. Preferably, the esterase is an intracellular esterase such that the chemical group is not removed until the pro-NAD agent is inside a cell.

In a preferred embodiment, $R_1$ is an unbranched or branched chain alkane, alkene or alkyne of 1 carbon to about 30 carbon atoms, such as, for example between about 14 and about 22 carbons. $R_1$ may also contain one or more functional groups. A functional group is an atom or group of atoms acting as a unit, that has replaced a hydrogen atom in a hydrocarbon molecule and whose presence imparts characteristic properties to a molecule. Examples of functional groups that can be used include thiol, alcohol, amine, carboxylic acid, onium, carboxylic anhydride, carboxylic ester, acyl halide, amide, nitrile, aldehyde, ketone, imines, ethers, sulfide, halide, nitro, nitroso, azides, diazo, and a combination of these groups.

In a preferred embodiment, $R_1$ may be a chemical group that changes the log $P_{o/w}$ of said pro-NAD agent to between about 5 to about 20.

In a preferred embodiment, the pro-NAD agent has a log $P_{o/w}$ range between about 5 to about 20. More preferably, the pro-NAD agent has a log $P_{o/w}$ range between about 10 to about 15.

For example, the pro-NAD agent may be methylnicotinate, ethylnicotinate, butylnicotinate, hexylnicotinate, octylnicotinate, tetradecylnicotinate, octadecylnicotinate or a combination of these chemicals. A combination may be, for example, at least one chemical selected from the group consisting of methylnicotinate, ethylnicotinate, butylnicotinate, hexylnicotinate, octylnicotinate and at least one chemical selected from the group consisting of tetradecylnicotinate and octadecylnicotinate.

Alternatively, the pro-NAD agent may comprise one or more compounds with the following formula:

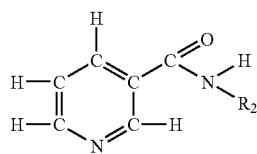

where $R_2$ is a hydrogen or a chemical group that can be enzymatically or chemically removed to generate nicotinamide after the pharmaceutical composition is administered. For example, $R_2$ may be a carboxylic acid containing an alkane, alkene or alkyne of about 1 to about 30 carbon atoms. Preferably, $R_2$ is a carboxylic acid containing an alkane R group with between 14 and 22 carbons. In addition $R_2$ also contains one or more functional groups. The functional group may be, for example, thiol, alcohol, amine, carboxylic acid, onium, carboxylic anhydride, carboxylic ester, acyl halide, amide, nitrile, aldehyde, ketone, imines, ethers, sulfide, halide, nitro, nitroso, azides, or diazo. Preferred functional groups include thiol, alcohol, amine, and carboxylic acid groups. $R_2$ may also have more than one functional group. Further, $R_2$ may be any chemical group that changes the log $P_{o/w}$ of said pro-NAD agent to between about 5 to about 20. Preferably, the pro-NAD agent has a log $P_{o/w}$ range between about 5 to about 20. More preferably, the pro-NAD agent has a log $P_{o/w}$ range between about 10 to about 15.

The pharmaceutical composition of the invention may have a pro-NAD agent concentration that is between about 0.001% to about 10% by weight. Preferably, the pro-NAD agent is between about 0.01% and about 3% by weight. The pharmaceutical composition may further comprise an optional agent such as, for example, antioxidants, sunscreens, vitamins, a pH stabilizer, or a combination of these agents.

It is understood that the pharmaceutical composition of the invention may be used for treating a subject. The subject is an animal. The animal may be a unicellular or a multicellular animal such as, for example, a mammal. Further, the mammal may be a human. The subject may also be a cultured cell population, a cultured cell line, an egg, a sperm or a zygote.

Another embodiment of the invention is directed to a method for treating or for slowing skin deterioration. In the method, a pharmaceutical composition of the invention may be administered to a subject to treat, slow or reverse skin deterioration in the subject. Preferably, the method will increase the skin cell intracellular NAD concentration by at least about 50% over an untreated subject. More preferably, the method will increase the intracellular NAD concentration by an even greater amount such as, for example, by 100% over an untreated subject. It is understood that skin cell in this application refers to fibroblasts and/or keratinocytes. The administration may be applied topically, intradermally or subcutaneously. Topical administration may be via dermal patch or slow release mechanism to the layer of skin of the mammal. In addition, the administration may be oral or parenteral.

Another embodiment of the invention is directed to a process for achieving transdermal delivery of a pro-NAD agent. In the process, an effective amount of a topical composition comprising an effective amount of one or more pro-NAD agent is applied to the skin of a subject. The pro-NAD agent used in this process may be any pro-NAD agent discussed in this application.

Another embodiment of the invention is directed to a process for reducing the cytotoxic effects of DNA damage in the skin of a mammal by enhancing or elevating one or more skin cell intracellular proteins. The skin cells are the fibroblasts and/or keratinocytes in the skin. The process comprises applying to a layer of skin of the mammal an effective amount of a pharmaceutical composition of the invention. The intracellular protein may be p53. Alternatively, the intracellular protein may be PARP-1, PARP-2, PARP-3, tankyrase, V-PARP and telomerase.

Another embodiment of the invention is directed to a method for treating skin in order to inhibit skin deterioration due to UV exposure. In the method, a pharmaceutical composition of the invention is applied to the skin at a time sufficiently close to the time of UV exposure to inhibit UV-induced damage to the skin. The pharmaceutical composition may be applied before UV exposure. Alternatively, the pharmaceutical composition maybe applied after UV exposure. The time of application may be for example, less than 1 hour, less than 2 hour, less than 6 hour, less than 12 hour or less than 1 day before UV exposure. Alternatively, the time of application may be, for example, less than 5 minutes, less than 10 minutes, less than 20 minutes, less than 1 hour, less than 2 hours, less than 6 hours, less than 12 hours, less than 1 day, less than 2 days, or less than 5 days after UV exposure.

Other embodiments and advantages of the invention are set forth, in part, in the description which follows and, in part, will be obvious from this description and understood by the skilled artisan practicing this invention.

DESCRIPTION OF THE DRAWINGS

FIG. 4 depicts the decreased cellular NAD content in both human fibroblasts and keratinocytes that results from decreased niacin status.

FIG. 9 Panel A depicts the cellular content of p53 as a function of cellular NAD content. Panel B depicts the relative content of p53 following genotoxic stress in cells with a low or normal NAD content.

DESCRIPTION OF THE INVENTION

Figure 1:
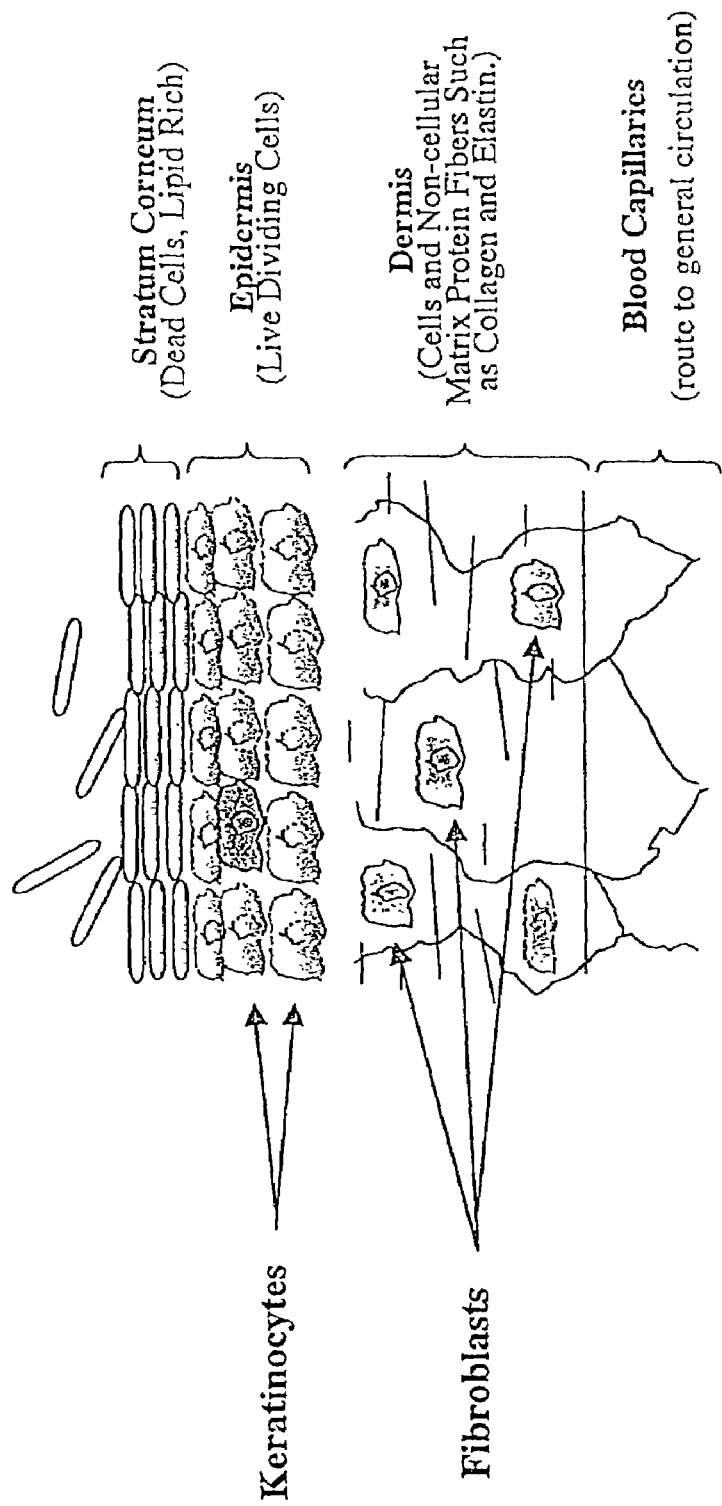
FIG. 1 depicts a diagram of skin marking the location of the two major cell types present in skin, namely fibroblasts located in the dermal layer of the skin and the keratinocytes located in the epidermal layer of the skin.
Figure 2:
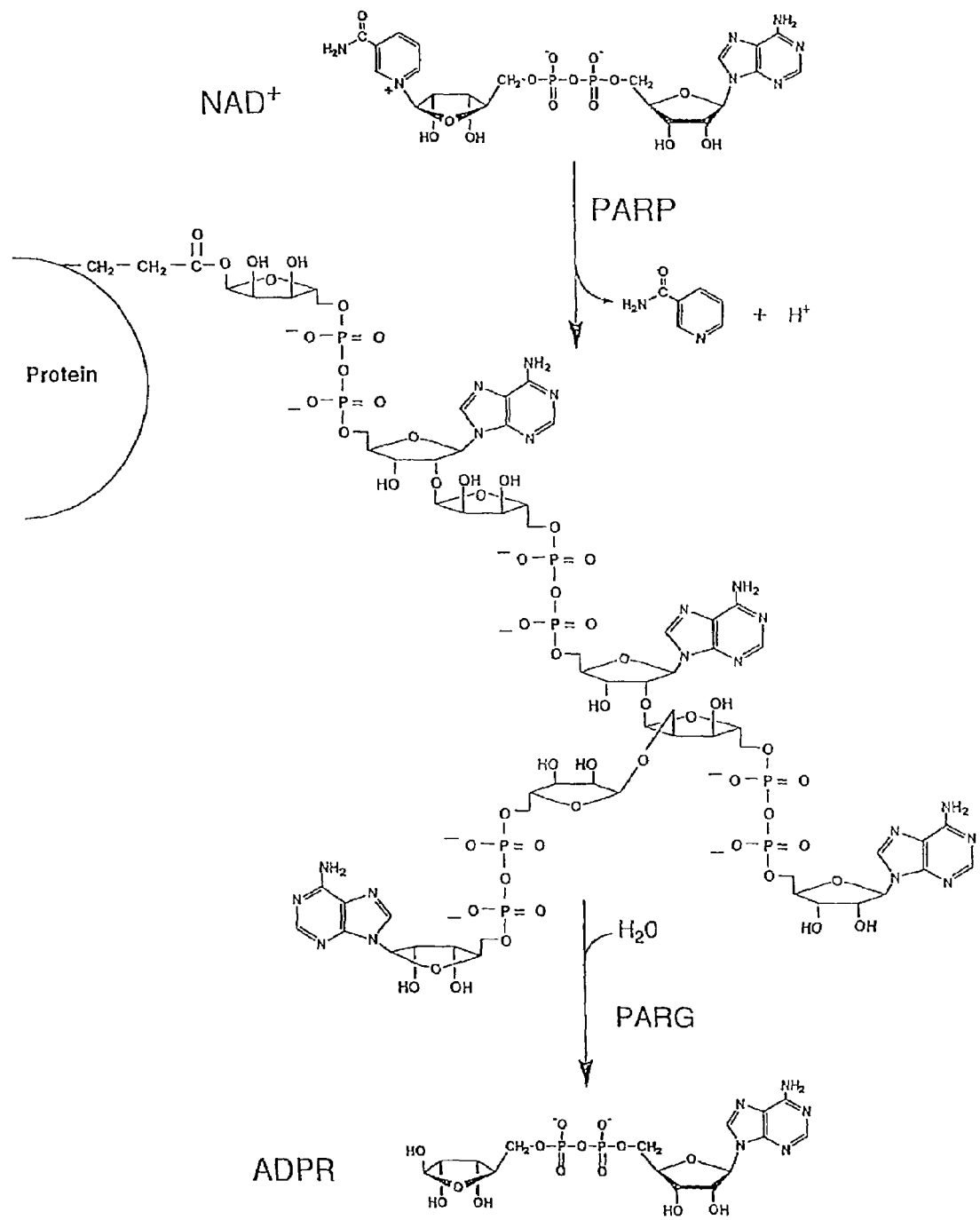
FIG. 2 depicts the reaction catalyzed by PARPs and the hydrolysis of ADPR polymers to free ADPR by poly(ADP-ribose) glycohydrolase (PARG).

NAD has a direct and central involvement in the mechanisms that maintain genomic integrity as the substrate for the synthesis of ADP-ribose (ADPR) polymers by the action of poly(ADP-ribose) polymerases (PARPs) (Jacobson, M. K. and Jacobson, E. L. (1999) Trends Biochem. Sci. 24, 415-417). The reaction catalyzed by PARPs and the hydrolysis of ADPR polymers to free ADPR by poly(ADP-ribose) glycohydrolase (PARG) is shown in FIG. 2. The involvement of PARPs and PARG in protective cellular responses to genotoxic stress is overviewed in FIG. 3. NAD is used by PARPs, in concert with other DNA damage response proteins such as p53 and DNA protein kinase to initiate DNA damage response signaling pathways that lead to DNA repair and cellular recovery of normal cell function. In addition to the DNA repair function of NAD, in cases where more DNA damage occurs, as might be experienced in skin cells following a severe sunburn, the DNA damage response proteins including PARPs can initiate response pathways that lead to programmed cell death, a process termed apoptosis. As this relates to skin, the apoptosis response has the effect of "erasing" badly damaged cells with the likely benefit of elimination of cells that may progress to cancer. Finally, massive doses of DNA damage lead to death by necrosis because the hyperactivation of PARPs results in depletion of the cellular NAD with a subsequent loss of all cellular energy-dependent functions. The extent of DNA damage that would result in necrosis is not likely to occur in normal skin but may occur in diseased skin or more likely in heart or brain tissue following heart attack or stroke.

Many enzymes that confer a protective cellular response to DNA damage utilize NAD. Of these enzymes, the best understood is PARP-1. The presence of DNA strand breaks strongly activates PARP-1 and many studies (reviewed in Pieper, A. A. et al. (1999) Trends Pharmacol. Sci. 4, 171-181) have provided evidence that, in concert with other DNA break sensing proteins such as p53 and DNA protein kinase, PARP-1 participates in modulating the response pathways depicted in FIG. 3.

Recently, another protein that uses NAD in response to DNA damage was discovered and termed PARP-2 (Berghammer, H. et al., (1999) FEBS Lett. 449,259-263; Johansson, M. (1999) Genomics 57, 442-445; Amé, J. C. et al. (1999) J. Biol. Chem. 274, 17860-17866). The nuclear location and activation of PARP-2 by DNA breaks suggest that it is also involved in the DNA response signaling pathways depicted in FIG. 3. The presence of an additional protein with high sequence homology to PARP-2 (Johansson, M. (1999) Genomics 57, 442-445) may represent yet another NAD utilizing enzyme involved in protective cellular responses.

Two other proteins with PARP activity have been recently discovered (Smith, S et al., (1998) Science 282, 1484-1487; Kickhoefer, V. A. et al. (1999) J. Cell Biol. 146:917-928). One of these PARPs, termed tankyrase, is a component of chromosome termini termed telomeres (Smith, S et al., (1998) Science 282, 1484-1487). Telomeres are the terminal regions of chromosomes that contain unique repetitive DNA sequences and G-rich single stranded overhangs. In most human cells, telomeres shorten with each round of cell division because the enzymes of DNA replication are unable to completely replicate the chromosome ends. This process, termed "telomere erosion," limits the proliferation potential of normal cells because telomeres erosion ultimately reaches a point where cells are no longer able to divide and this accounts for cellular aging. Thus, optimal levels of NAD in the cell also facilitate the maintenance of telomeres and thus retard cell aging. Another PARP (Vault-PARP) has been recently identified as one of three proteins present in vaults, large ribonucleoprotein complexes of unknown function located primarily in the cytoplasmic compartment (Kickhoefer, V. A. et al. (1999) J. Cell Biol. 146:917-928). Vault-PARP also occurs in the mitotic spindle of chromosomes. Thus, NAD may function in the maintenance of genomic integrity by serving as the substrate for Vault PARP.

The involvement of PARP-1, PARP-2 and PARP-3, in protective cellular responses to genotoxic stress demonstrates a requirement for NAD in protective responses that repair or erase damage as appropriate. While NAD is an essential component of many cellular and DNA repair pathways, it was not clear from the prior art how these DNA repair pathways are controlled.

As shown in the Examples section, it has been found that surprisingly, NAD is a limiting factor in the cellular response to genomic damage. The invention described here relates to (1) the discovery that protective cellular responses involving NAD are strongly dependent upon the NAD content of the cell at the time of the genotoxic stress; (2) that the NAD content of skin cells can be elevated by topical application of specific bioactive molecules; (3) that the elevation of intracellular NAD levels enhances the cellular DNA repair mechanism. These findings are discussed in the Example section.

One embodiment of the invention is directed to a pharmaceutical composition for a mammal in need of an elevation of intracellular NAD content. The pharmaceutical composition comprises a pro-NAD agent at a concentration sufficient to elevate intracellular NAD content and a pharmaceutically acceptable carrier.

Pharmaceutical composition refers to a composition suitable for pharmaceutical use in an animal or animal cell line. The animal may be a mammal, such as a human. A pharmaceutical composition of the invention comprises a pharmaceutically effective amount of a pro-NAD agent and a pharmaceutically acceptable carrier. "Pharmaceutically effective amount" refers to that amount of an agent effective to produce the intended effect of reducing, preventing and/or reversing skin deterioration. Skin deterioration may be caused by a number of environmental factors enumerated in the background section. Such factors include ultraviolet radiation sources such as sunlight, chemicals, and pollution. Other factors that cause skin deterioration include reactive oxygen species that are generated by environmental insults and/or metabolism.

The term "pro-NAD agent" refers to compounds which are NAD precursors which, following administration to a subject and subsequent absorption, are converted to an active species in vivo via some process, such as a metabolic process. Other products from the conversion process are easily disposed of by the body. More preferred pro-NAD agents produce products from the conversion process which are generally accepted as safe.

Pharmaceutically acceptable carriers may be any carrier known in the field as suitable for pharmaceutical (i.e., topical, oral, and parenteral) application. Suitable pharmaceutical carriers and formulations are described, for example, in Remington's Pharmaceutical Sciences (19th ed.) (Genarro, ed. (1995) Mack Publishing Co., Easton, Pa.). Preferred pharmaceutical carriers depend upon the intended mode of administration of the active agent. Typical modes of administration include enteral (i.e., oral) or parenteral (i.e., subcutaneous, intramuscular, or intravenous intraperitoneal injection); or topical (transdermal, or transmucosal administration).

The pharmaceutically acceptable carrier may include, for example, emollients, humectants, thickeners, silicones and water. Suitable formulations that include pharmaceutically acceptable excipients for introducing pro-NAD agents to the bloodstream by other than injection routes can be found in Remington's Pharmaceutical Sciences (19th ed.) (Genarro, ed. (1995) Mack Publishing Co., Easton, Pa.). Specific examples of carriers include hydrocarbon oils and waxes such as mineral oil, petrolatum, paraffin, ceresin, ozokerite, microcrystalline wax, polyethylene, and perhydrosqualene; triglyceride such as vegetable oil, animal fats, castor oil, cocoa butter, safflower oil, cottonseed oil, corn oil, olive oil, cod liver oil, almond oil, avocado oil, palm oil, sesame oil, squalene, and maleated soybean oil; acetoglycerides, such as acetylated monoglycerides; ethoxylated glycerides, such as ethoxylated glyceryl monostearate; alkyl esters of fatty acids such as methyl, isopropyl, and butyl, hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate esters of fatty acid; alkenyl esters of fatty acids such as oleyl myristate, oleyl stearate, and oleyl oleate; fatty acids such as pelargonic, lauric, myristic, palmitic, stearic, isostearic, hydroxystearic, oleic, linoleic, ricinoleic, arachidic, behenic, and erucic acids; fatty alcohols such as lauryl, myristyl, cetyl, hexadecyl, stearyl, isostearyl, hydroxystearyl, oleyl, ricinoleyl, behenyl, erucyl, and 2-octyl dodecanyl alcohols; fatty alcohol ethers such as lauryl, cetyl, stearyl, isostearyl, oleyl, and cholesterol alcohols, having attached thereto from 1 to 50 ethylene oxide groups or 1 to 50 propylene oxide groups; ether-esters such as fatty acid esters of ethoxylated fatty alcohols; lanolin and derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases; polyhydric alcohol esters such as ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 mono-oleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid esters, sorbitan fatty acid esters, and polyoxyethylene sorbitan fatty acid esters are satisfactory polyhydric alcohol esters; waxes such as beeswax, spermaceti, myristyl myristate, stearyl stearatepolyoxyethylene sorbitol beeswax, carnauba and candelilla waxes; phospholipids such as lecithin and derivatives; sterols such as cholesterol and cholesterol fatty acid esters, amides such as fatty acid amides, ethoxylated fatty acid amides, and solid fatty acid alkanolamides.

In addition, the pro-NAD agent and the pharmaceutically acceptable carrier may be enclosed in a hard or soft shell gelatin capsule, compressed into tablets, or incorporated directly into the individual's diet. Specifically, the pro-NAD agent may be incorporated with excipients and used in the form of ingestible tablets, buccal tablets, troches, capsules, elixirs, suspensions, syrups, wafers, and the like. When the pro-NAD agent is administered orally, it may be mixed with other food forms and pharmaceutically acceptable flavor enhancers. When the pro-NAD agent is administered enterally, they may be introduced in a solid, semi-solid, suspension, or emulsion form and may be compounded with any number of well-known, pharmaceutically acceptable additives. Sustained release oral delivery systems and/or enteric coatings for orally administered dosage forms are known in the art and also contemplated.

The pharmaceutical composition may be administered orally, topically or parenterally. Oral administration refers to the administration of the formulation via the mouth through ingestion, or via any other part of the gastrointestinal system including the esophagus or through suppository administration. Parenteral administration refers to the delivery of a composition, such as a composition comprising a pro-NAD agent by a route other than through the gastrointestinal tract (e.g., oral delivery). In particular, parenteral administration may be via intravenous, subcutaneous, intramuscular or intramedullary (i.e., intrathecal) injection. Topical administration refers to the application of a pharmaceutical agent to the external surface of the skin or the mucous membranes (including the surface membranes of the nose, lungs and mouth), such that the agent crosses the external surface of the skin or mucous membrane and enters the underlying tissues. Topical administration of a pharmaceutical agent can result in a limited distribution of the agent to the skin and surrounding tissues or, when the agent is removed from the treatment area by the bloodstream, can result in systemic distribution of the agent. In a preferred form of topical administration, the pharmaceutical agent is delivered by transdermal delivery. Transdermal delivery refers to the diffusion of an agent across the barrier of the skin. The skin (stratum corneum and epidermis) acts as a barrier and few pharmaceutical agents are able to penetrate intact skin. In contrast, the dermis is permeable to many solutes and absorption of drugs therefore occurs more readily through skin which is abraded or otherwise stripped of the epidermis to expose the dermis. Absorption through intact skin can be enhanced by placing the active agent in an oily vehicle before application to the skin (a process known as inunction). Passive topical administration may consist of applying the active agent directly to the treatment site in combination with emollients or penetration enhancers.

It will be appreciated that the unit content of active ingredient or ingredients contained in an individual dose of each dosage form need not in itself constitute an effective amount since the necessary effective amount can be reached by administration of a plurality of dosage units (such as capsules or tablets or combinations thereof). That is, the individual dose of oral pro-NAD agents need not provide sufficient elevation of intracellular NAD content. However, the continued dosage of oral pro-NAD agent over a period of time will result in an elevated intracellular NAD level. Similarly, an individual topical application of the pro-NAD agent may not elevate the skin cell intracellular NAD content to the desired level. However, the repeated application of the pro-NAD agent over a period of time will result in skin cells with elevated NAD content.

In a preferred embodiment, the pro-NAD agent contains one or more pro-NAD agents with the following formula:

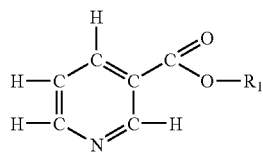

$R_1$ may be a hydrogen or any group that can be enzymatically or chemically removed to generate nicotinic acid following administration. For example, $R_1$ may be an unbranched (i.e. straight or branched chain alkane, alkene or alkyne of up to 30 carbon atoms in length. For example, if $R_1$ is an unbranched alkane, it would have the formula —$(CH_2)_n$—$CH_3$, wherein n can be any integer from 0 to 29. $R_1$ may contain other functional groups such as, for example, OH groups, SH groups, COOH groups, $NH_2$ and the like. Specific examples of preferred pro-NAD agents include methylnicotinate, ethylnicotinate, butylnicotinate, hexylnicotinate, octylnicotinate, tetradecylnicotinate, octadecylnicotinate. In a preferred embodiment, the pro-NAD agent has an octanol/water partition coefficient range wherein log $P_{o/w}$ is between about 5 to about 20, more preferably between 10 and 15. Thus, $R_1$ comprising a straight chain alkane of 14 to 22 carbons (i.e., 14, 15, 16, 17, 18, 19, 20, 21 or 22 carbons) with log $P_{o/w}$ values between 10 and 15 are most preferred.

In another preferred embodiment, the pro-NAD agent contains one or more pro-NAD agents with the following formula:

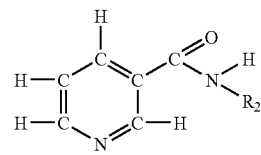

where $R_2$ may be a hydrogen or any group that can be enzymatically or chemically removed to generate nicotinamide following administration. For example, $R_2$ may be a carboxylic acid compound of the formula $R_1$—COOH wherein $R_1$ is as described above, and wherein said $R_2$ is linked in an amide linkage as shown below:

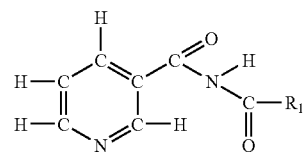

In a preferred embodiment, this class of pro-NAD agents has an octanol/water partition coefficient ($P_{o/w}$) range between $\log(P_{o/w})$ of about 5 to about 20; more preferably between about 10 to about 15.

It is understood that the pro-NAD agent may comprise any combination of the preferred pro-NAD agents listed above. Thus, for example, the pharmaceutical composition may comprise tetradecylnicotinate, octadecylnicotinate or a combination of both chemicals. As another example, the pharmaceutical composition may contain one or more nicotinic acid derivative with one or more compounds selected from nicotinamide or nicotinamide derivatives. As another example, the pharmaceutical composition may comprise one or more pro-NAD agents selected from the group consisting of methylnicotinate, ethylnicotinate, butylnicotinate, hexylnicotinate, octylnicotinate and one or more pro-NAD agents selected from the group consisting of tetradecylnicotinate and octadecylnicotinate. It is also understood that the pro-NAD agent may be a salt of the agents listed in this application. Preferably the salt is administered in soluble form.

Effective Dosage:

Pharmaceutical compositions suitable for use in the present invention include compositions wherein the active ingredients are contained in an effective amount to achieve its intended purpose. More specifically, a therapeutically effective amount means an amount effective to optimally elevate the skin cell NAD content to prevent development or to alleviate the existing symptoms of skin deterioration. It is understood that at some dosage levels, an effective amount may not show any measurable effect until after a week, a month, three months, or six months of usage. Further, it is understood that an effective amount may lessen the rate of the natural deterioration that comes with age but not reverse the deterioration that has already occurred. Determination of the effective amounts is well within the capability of those skilled in the art, especially in light of the detailed disclosure provided herein.

It is understood, however, that the specific dose level for any particular user will depend upon a variety of factors including the activity of the specific pro-NAD agent employed, the age, the physical activity level, general health, and the severity of the skin problem. For example, an active person who perspires may require a more oily or waterproof formulation. A person with dry skin will require a more oily formulation while a person with oily skin may prefer a less oily suspension.

For any pro-NAD agent used in the method of the invention, the therapeutically effective dose can be estimated initially from cell culture assays or from animal testing. For example, a dose may be formulated in an animal skin test model to increase cellular NAD level by, for example, about 50%, about 100%, about 150%, about 200%, about 300% or about 500% over the normal NAD level. Such information can be used to more accurately determine the useful dose in a human.

A therapeutically effective dose also refers to that amount of the pro-NAD agent (or agents) that results in elevation of skin cell NAD content with amelioration of symptoms without unwanted or intolerable side effects. Toxicity and therapeutic efficacy of the pro-NAD agent can be determined by standard pharmaceutical procedures in cell cultures or experimental animals. Using standard methods, the dosage that shows effectiveness in about 50% of the test population, the $ED_{50}$, may be determined. Effectiveness may be any sign that the symptoms of skin deterioration (loss of moisture, fine lines, deep lines, wrinkles, and loss of elasticity as well as atrophic sclerosis and other blemishes of skin) are slowed, reduced, or reversed. Similarly, the dosage that produces an undesirable side effect to 50% of the population, the $SD_{50}$, can be determined. Undesirable side effects include death, burns, wounds, rashes, abnormal redness and the like. The dose ratio between side effect and therapeutic effects can be expressed as the therapeutic index and it can be expressed as a ratio between $SD_{50}$ and $ED_{50}$ (i.e., therapeutic index $=SD_{50}/ED_{50}$). Pro-NAD agents with high therapeutic indexes are preferred. That is, pro-NAD agents that are effective at low dosage and which do not have undesirable side effects until very high doses are preferred. A preferred therapeutic index is greater than about 3, more preferably, the therapeutic index is greater than 10, most preferably the therapeutic index is greater than 25, such as, for example, greater than 50. Furthermore, pro-NAD agents that do not have side effects at any dosage levels are more preferred. Finally, pro-NAD agents that are effective at low dosages and do not have side effects at any dosage levels are most preferred. The exact formulation, route of administration and dosage can be chosen depending on the desired effect and can be made by those of skill in the art. For example, a skin cream for maintenance of youthful looking skin may have a lower dosage than a skin cream for the repair of sun or age damaged skin.

Dosage intervals can be determined by experimental testing. Pro-NAD agents should be administered using a regimen which maintains dermal cellular levels at about 50% above normal, about 100% above normal, preferably about 200% above normal, more preferably about 300% above normal and most preferably about 500% above normal skin cell samples not exposed to pro-NAD agents. The amount of NAD elevation will, of course, be dependent on the subject being treated, on the subject's exposure to the environment, the severity of the damage to the skin, and the manner and composition of the composition. For example a fair skinned subject, an older subject or a subject with a high degree of sun exposure at work may require more NAD elevation.

In a preferred embodiment, the pharmaceutical composition of the invention may comprise a pro-NAD agent at a concentration of between about 0.001% to about 10%, preferably between about 0.01% and about 3%, such as, for example, about 1% by weight.

Optional Agents:

The composition of the invention may optionally comprise other agents known to have a cosmetic or beneficial effect on the skin. Such agents include, for example, antioxidants, sunscreens, a pH buffer and a combination thereof. While any antioxidant that is chemically compatible may be used, preferred antioxidants include amino acids such as glycine, histidine, tyrosine, and tryptophan; imidazoles such as urocanic acid; peptides such as D,L-carnosine, D-carnosine, L-carnosine and anserine; carotenoids; carotenes such as alpha-carotene, beta-carotene, and lycopene; lipoic acid such as dihydrolipoic acid; thiols such as aurothioglucose, propylthiouracil, thioredoxin, glutathione, cysteine, cystine, and cystamine; dilauryl thiodipropionate; distearyl thiodipropionate; thiodipropionic acid; sulphoximine compounds such as buthionine-sulphoximines, homocysteine-sulphoximine, buthionine-sulphones, penta-, hexa- and heptathionine-sulphoximine; metal chelating agents such as alpha-hydroxyfatty acids, palmitic acid, phytic acid, lactoferrin EDTA and EGTA; alpha-hydroxy acids such as citric acid, lactic acid, and malic acid; unsaturated fatty acids such as gamma-linolenic acid, linoleic acid and oleic acid; folic acid; ubiquinone and ubiquinol; vitamin C and derivatives such as ascorbyl palmitate, Mg ascorbyl phosphate and ascorbyl acetate; tocopherols and derivatives such as vitamin E acetate; vitamin A and derivatives such as vitamin A palmitate; coniferyl benzoate of benzoin resin; rutic acid; alpha-glycosylrutin; ferulic acid; furfurylideneglucitol; carnosine; butylhydroxytoluene; butylhydroxyanisole; nordihydroguaiac resin acid; nordihydroguaiaretic acid; trihydroxybutyrophenone; uric acid; mannose; zinc compounds such as ZnO, $ZnSO_4$; selenium; and stilbenes. In addition the antioxidant may include derivatives such as salts, esters, ethers, peptides, lipids, nucleotides, nucleosides of said antioxidants. The derivatives may include, for example, glycosyl, N-acetyl, methyl, ethyl, propyl, amyl, butyl and lauryl, palmitoyl, oleyl, γ-linoleyl, cholesteryl and glyceryl esters derivatives. Further, the antioxidants may be a combination, a physical blend, of salts of one or more antioxidants.

The amount of the abovementioned antioxidants (one or more compounds) in the formulations is preferably 0.001 to 30% by weight, particularly preferably 0.05-20% by weight, in particular 1-10% by weight, based on the total weight of the formulation.

Another optional agent is a sunblock. Sunblocks are any chemicals that can reduce ultraviolet light absorption by the skin. Sunblock may scatter, absorb or reflect ultraviolet radiation. The addition of a sunblock allows the cooperative and synergistic operation of the pro-NAD agent and provides added convenience for the consumer.

The specific type of sunblock is limited to those that will not interfere with the NAD promoting function of the pro-NAD agents. Sunblocks and ultraviolet light absorbing, reflecting, and scattering chemicals are known to those of skill in the art. Accordingly, while a number of sunblocks are listed below, the methods and compositions of the invention are not limited to these sunblocks. Chemicals that are useful as sunblocks comprise dioxybenzone, ethyl 4-[bis(hydroxypropyl)] aminobenzoate, glyceryl aminobenzoate, homosalate, menthyl anthranilate, octocrylene, octyl methoxycinnamate, octyl salicylate, oxybenzone, padimate O, red petrolatum, titanium dioxide, 4-menthylbenzylidene camphor, benzophenone-1, benzophenone-2, benzophenone-6, benzophenone-12, isopropyl dibenzoyl methane, butyl methoxydibenzoylmethane, zotocrylene, zinc oxide, para-aminobenzoic acid (PABA), cinnamate and derivatives, analogs and functional analogs of said chemicals. Sunblocks may also be physical blends or chemical combinations of one or more individual chemicals.

Optional pH buffers (pH stabilizers) include any known chemicals suitable for maintaining pH in a pharmaceutical composition. Such chemicals are known are listed, for example, in standard chemistry texts (e.g., Scopes, Protein Purification, Springer-Verlag, New York, N.Y. (1988); see, e.g., page 243).

In another embodiment, the composition may optionally comprise a topically active drug such as antifungal compounds; antibacterial compounds; anti-inflammatory compounds; topical anesthetics; skin disease and dermatitis medications; and anti-itch and irritation-reducing compounds; analgesics; antibiotics; antiseptics; antiparasitics. Further, the composition may comprise a dermatological drug such as an anti acne preparations; anti-inflammatory agents; depigmenting agents, such as monobenzone; dermatitis relief agents, such as the active steroid amcinonide, diflorasone diacetate, hydrocortisone, and the like; diaper rash relief agents, such as methylbenzethonium chloride and the like; emollients and moisturizers, such as mineral oil, PEG-4 dilaurate, lanolin oil, petrolatum, mineral wax and the like; fungicides, such as butocouazole nitrate, haloprogin, clotrimazole, and the like; herpes treatment drugs, such as O-[(2-hydroxyethoxy)-methyl]guanine; pruritic medications, such as alclometasone dipropionate, betamethasone valerate, isopropyl myristate MSD, and the like; psoriasis, seborrhea and scabicide agents, such as anthralin, methoxsalen, coal tar and the like; steroids, such as 2-(acetyloxy)-9-fluoro-1',2',3',4'-tetrahydro-11-hydroxypregna-1,4-dieno[16,17-b]naphthalene-3,20-dione and 21-chloro-9-fluoro-1',2',3',4'-tetrahydro-11b-hydroxypregna-1,4-dieno[16z,17-b]naphthalene-3,20-dione. Any other medication which is compatible with pro-NAD agents and which is effective when administered topically can be incorporated into the method and composition of the present invention.

Although a method comprising applying a simple solution of one or more pro-NAD agent in water regularly to skin is effective to promote DNA repair and preventing skin deterioration, additional ingredients may be mixed with the active ingredients to an improved cosmetic effect, application effectiveness or as a diluent for the active ingredients.

For example, stearyl alcohol may be added to provide a lubrication effect up to a concentration of about 15 weight percent. Cetyl alcohol may be added as an emulsifying and thickening agent at a concentration of up to about 6 weight percent. Glycerin may be added as an emollient and humectant at a concentration of up to 18 weight percent. A mixture of cetyl esters wax, stearyl alcohol, cetyl alcohol, and glycerin may form a moisturizing cream base, diluent and carrier for the active ingredients. In addition to the primary active ingredient, one or more pro-NAD agent, there may be optional active ingredients that may comprise, for example, sunscreens, medications, antioxidants and the like.

In addition, preservatives and buffers may be added to prevent spoilage and maintain pH. Preservatives may include, for example, methyl paraben, propyl paraben, Quaternium-15. In addition, sodium lauryl sulfate may be added as a wetting and emulsifying agent. Finally, de-ionized water may be use as a diluent, carrier, and moisturizer.

Packaging:

The composition may, if desired, be presented in a pack of dispenser device which may contain one or more dosage units. The pack may, for example, be a container with a pump dispenser wherein each pump will produce a measured dosage of the composition. As another example, the composition may be individually foil or plastic wrapped in single dose packages. Photosensitive ingredients may be protected by opaque packages and heat sensitive ingredients may be refrigerated as is known in the art.

In another embodiment, the invention is directed to a method for treating or slowing skin deterioration. In the method, a pharmaceutical composition comprising a pro-NAD agent of the invention is administered to a subject in need of an intracellular elevation of NAD content. The method may increase intracellular NAD concentration by at least about 50%, preferable by at least about 100%, more preferably at least about 200% or about 300%, such as, for example, about 500% over NAD levels in untreated skin prior to treatment.

The pharmaceutical composition of the invention may be administered orally, topically or parenterally. For example, the administration maybe intradermal, subcutaneous, or via dermal patch or slow release mechanism to the layer of skin of the mammal.

Another embodiment of the invention is directed to a process for achieving transdermal delivery of a pro-NAD agent to the skin. In the process, a pharmaceutical composition containing one or more pro-NAD agents of the invention including agents with the following formula:

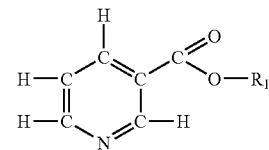

wherein $R_1$ may be a hydrogen or any group that can be enzymatically or chemically removed to generate nicotinic acid following administration. For example, $R_1$ maybe a straight or branched chain alkane, alkene or alkyne of up to 30 carbon atoms in length. For example, if $R_1$ is an unbranched (straight) alkane, it would have the formula $—(CH_2)_n—CH_3$, wherein n can be any integer from 0 to 29. $R_1$ may contain other functional groups such as, for example, OH groups, SH groups, COOH groups, $NH_2$ groups and the like. Specific examples of preferred pro-NAD agents include methylnicotinate, ethylnicotinate, butylnicotinate, hexylnicotinate, octylnicotinate, tetradecylnicotinate, octadecylnicotinate. In a preferred embodiment, the pro-NAD agent has an octanol/water partition coefficient range wherein log $P_{o/w}$ is between about 5 to about 20, more preferably between 10 and 15. Thus, $R_1$ comprising a straight chain alkane of 14 to 22 carbons (i.e., 14, 15, 16, 17, 18, 19, 20, 21 or 22 carbons) with log $P_{o/w}$ values between 10 and 15 are most preferred.

In another preferred embodiment, the pro-NAD agent may contain one or more pro-NAD agents with the following formula:

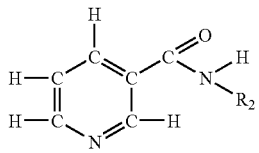

where $R_2$ may be a hydrogen or any group that can be enzymatically or chemically removed to generate nicotinamide following administration. For example, $R_2$ may be a carboxylic acid compound of the formula R1-COOH wherein $R_1$ is as described above, and wherein said $R_2$ is linked in an amide linkage as shown below:

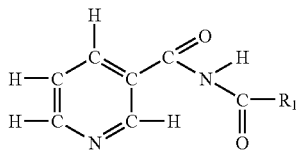

In a preferred embodiment, this class of pro-NAD agents has an octanol/water partition coefficient ($P_{o/w}$) range between log $P_{o/w}$ of about 5 to about 20; more preferably between about 10 to about 15.

Another embodiment of the invention is directed to a process for reducing the cytotoxic effects of DNA damage in the skin of a mammal by enhancing one or more enzymes comprising the step of applying to a layer of skin of said mammal an effective amount of a pharmaceutical composition comprising a pro-NAD agent, at a concentration sufficient to reduce the cytotoxic effects of DNA damage, and a pharmaceutically acceptable carrier. The enzyme to be enhanced by the pro-NAD agent may be, for example, P53, PARP-1, PARP-2, PARP-3, tankyrase, and V-PARP.

The methods, pharmaceutical compositions, and pro-NAD agents of this invention may be used to treat any biological subject. The term "subject" refers to an animal, or to one or more cells derived from an animal. Preferably, the animal is a mammal, most preferably a human. Cells may be in any form, including but not limited to cells retained in tissue, cell clusters, immortalized cells, transfected or transformed cells, and cells derived from an animal that have been physically or phenotypical altered. In an embodiment, the methods and pro-NAD agents may be used to treat tissue culture cells, such as, for example, embryonic stem cells or lymphocytes to prevent DNA damage. This may be used for example, to prevent bone marrow cells from mutating in a bone marrow transplant. Pro-NAD agents may also be used, for example, to keep sperm, eggs, and zygotes from mutating during in vitro fertilization procedures.

Other embodiments and advantages of the invention are set forth, in part, in the Examples which follows and, in part, will be obvious from this description and may be learned from the practice of the invention.

EXAMPLE 1

Sub-Optimal Niacin Status Results in Skin Cells with Reduced NAD Content

The effect of culture media containing sub-optimal precursors of NAD on the NAD content of normal human fibroblasts and keratinocytes was examined. Briefly, normal human fibroblasts were cultured with 5% $CO_2$ in nicotinamide supplemented medium or nicotinamide deficient medium. The nicotinamide deficient media used was Dulbecco's Modified Eagle Medium (DMEM) made without nicotinamide supplemented with 5% bovine senim. It may be made in the laboratory and is also available by custom ordered from commercial suppliers such as Life Technologies, Inc. (Rockville, Md.) or Sigma (St. Louis, Mo.). Nicotinamide supplemented medium is nicotinamide deficient media with supplemented with nicotinamide to 33 µM. After growth of the cells for several days, cells were extracted and analyzed for NAD content. The results of a typical experiment, showing that sub-optimal niacin status results in a decreased cellular NAD content in both human fibroblasts and keratinocytes are shown in FIG. 4.

Figure 5:
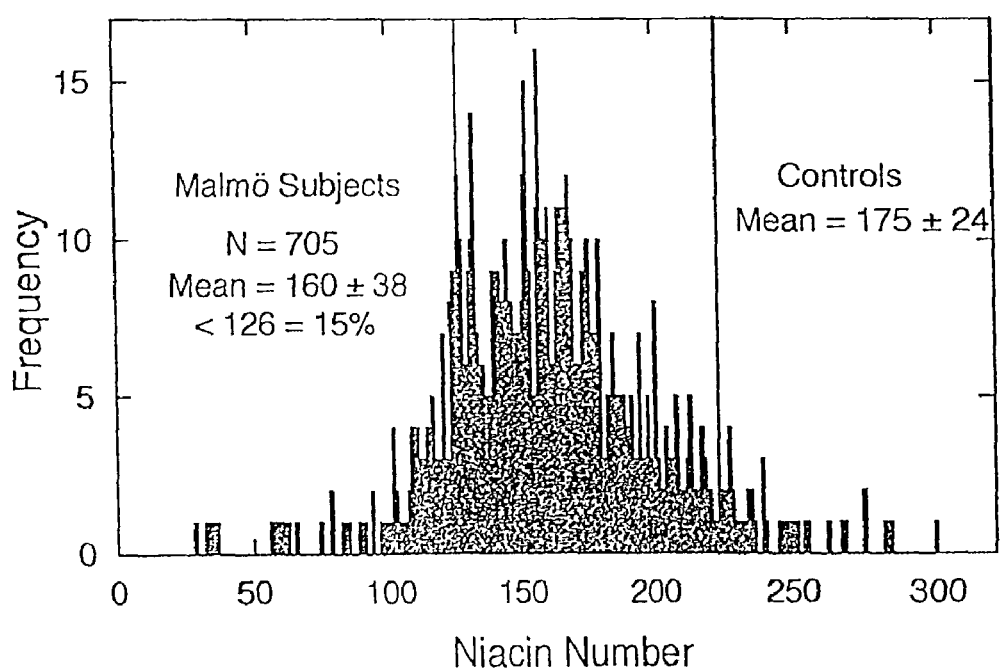
FIG. 5 depicts a distribution of niacin number values in a population of 705 subjects in Malmö, Sweden.

General niacin status varies widely in the human population. A biochemical assay of niacin status (Jacobson, E. L. and Jacobson, M. K., (1997) Methods in Enzymology, vol 280, Academic Press, New York, 221-230) has been used to assess the niacin status of a human population in Malmö, Sweden. In this assay, niacin status of individuals is determined by the ratio of NAD to NADP in red blood cells. This ratio multiplied by a factor of one hundred is referred to a "niacin number." Methods for measuring niacin content (niacin status) are disclosed in Jacobson, E L, and Jacobson, M K (*Meth Enzymol* 280, 221-230, 1997) and Jacobson, E L et al. (*J Cell Physiol* 99, 417-426, 1979) incorporated herein by reference. FIG. 5 shows a distribution of niacin number values in a population of 705 subjects in Malmö, Sweden. The values for a control group are also shown. The bars in FIG. 5 represent the range for 95.5% of the control group. The results show that the general niacin status varies widely in a human population and that 15% of these individuals have niacin number values that classify them as severely niacin deficient.

EXAMPLE 2

Increased NAD Content of Skin Correlates with Less Severe Skin Deterioration

Figure 6:
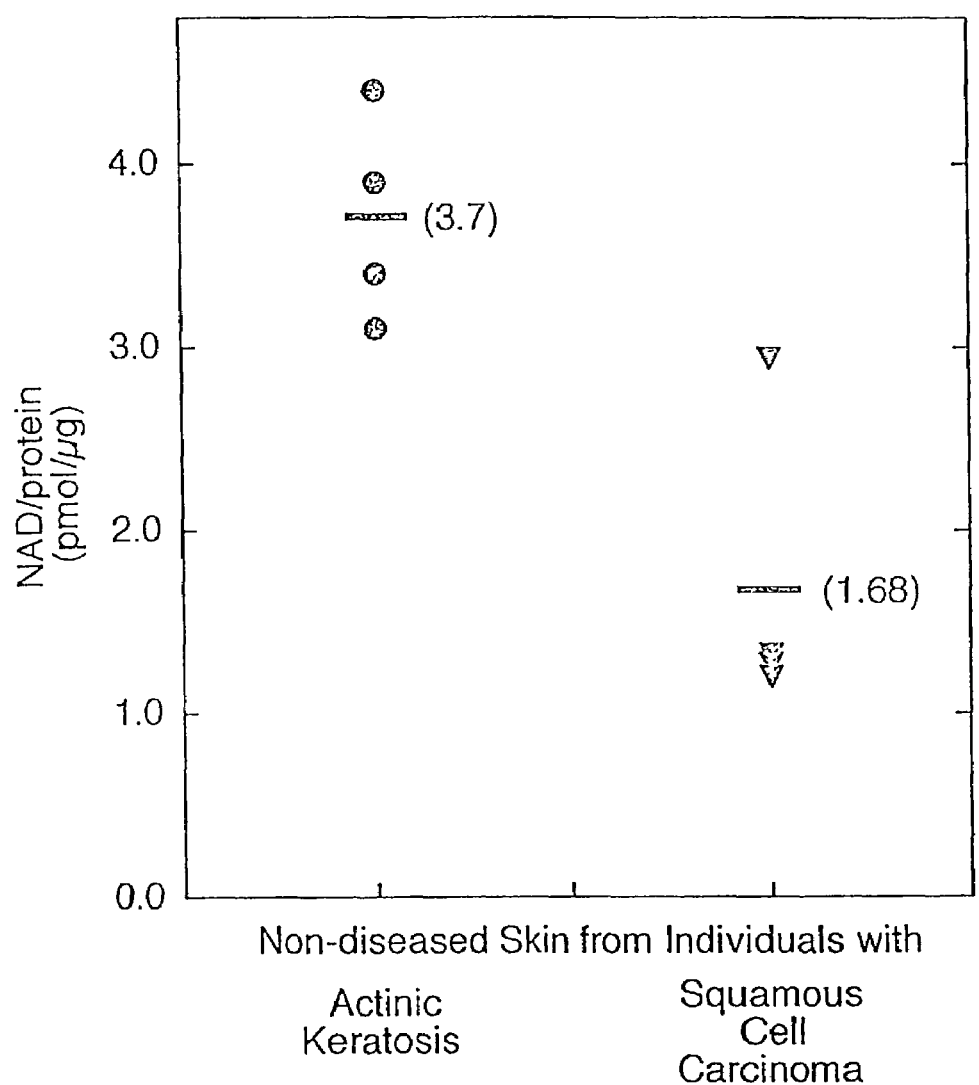
FIG. 6 depicts the NAD content of non-diseased skin from individuals with severely deteriorated skin (squamous cell carcinoma) and mildly deteriorated skin (actinic keratosis).

Since the NAD content of red blood cells varies widely within the human population, the possibility that the NAD content of skin cells varies widely was examined in experiments that addressed two questions related to skin cell NAD content. The first question addressed whether the NAD content of human skin shows significant variation. Non diseased areas of skin were taken from normal human volunteers and assayed for NAD content. The data of FIG. 6 shows that skin taken from non-diseased areas of normal human volunteers varies more than 4-fold in NAD content.

The next experiment was designed to address the question of whether a correlation exists between skin cell NAD content and susceptibility to skin deterioration. In this experiment, non diseased areas of skin from individuals with lesser deterioration were compared for NAD content with non diseased areas of skin from individuals with greater deterioration. The results, shown in FIG. 6, demonstrate that the NAD content of non-diseased skin from individuals with more serve skin deterioration (squamous cell carcinoma) had a significantly lower NAD content than skin derived from non-diseased skin from individuals with less severe skin deterioration (actinic keratosis).

EXAMPLE 3

Determining the Correlation Between DNA Repair Proficiency and NAD Content

Since the NAD content of human skin cells varies widely, a series of experiments was performed to examine DNA repair and DNA damage response proficiency of skin as a function of NAD content. The ability of cells to recover from the cell killing effects of genotoxic stress depend upon their ability to repair DNA damage and activate multiple DNA damage response pathways in response to genotoxic stresses. Briefly, normal human skin fibroblasts and human skin keratinocytes were cultured in control or suboptimal niacin medium (i.e. nicotinamide deficient media of Example 1) as described for Example 1 above. This results in cells with normal or depleted NAD content. Cells were then exposed to solar simulated sunlight and the ability of the cells to recover from the different doses of sunlight was determined by measuring growth of the cells 5 days following sunlight exposure.

Figure 7:
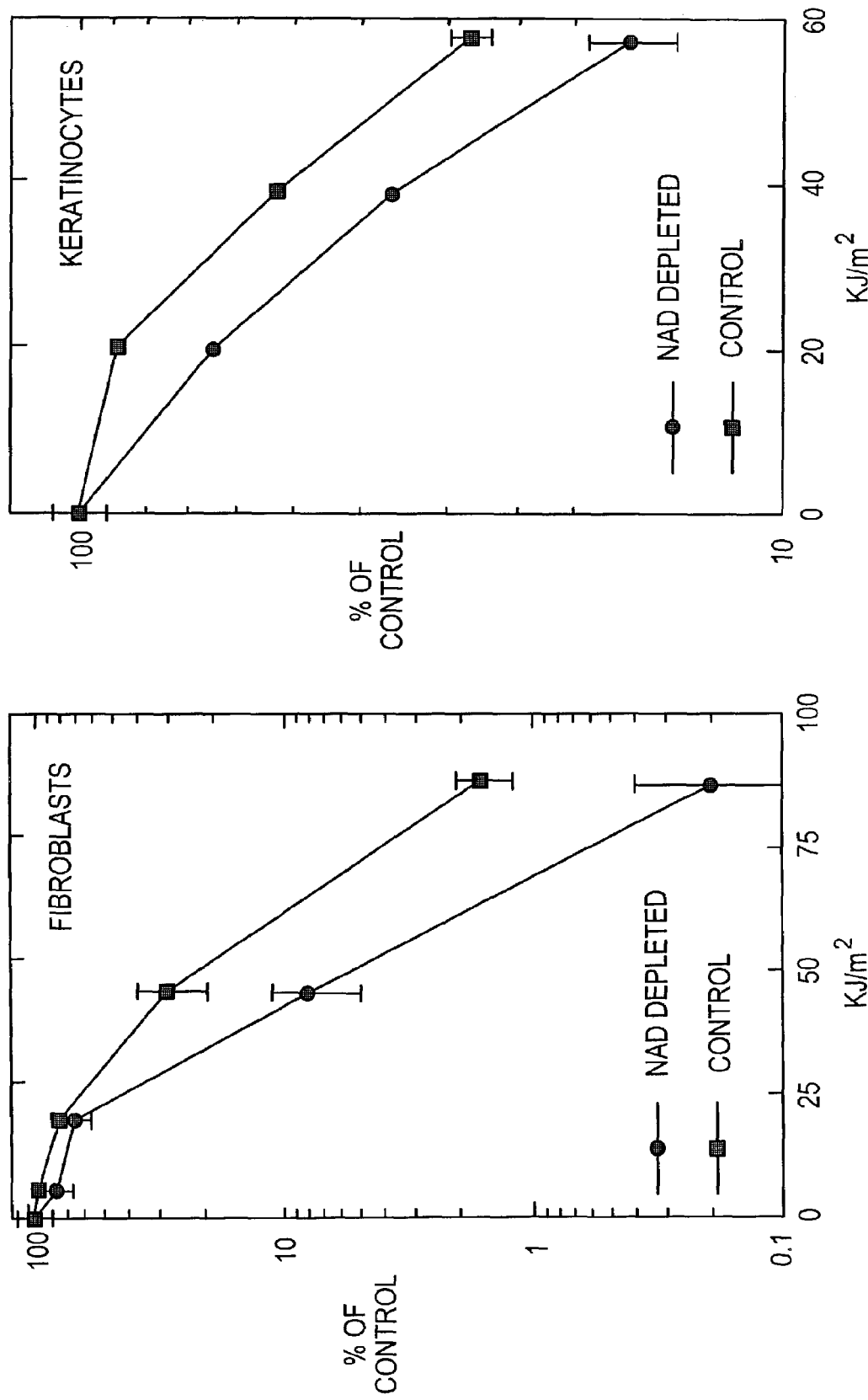
FIG. 7 depicts the recovery of human skin fibroblasts and human skin keratinocytes with a reduced NAD after exposure to solar radiation provided by a solar simulator.

FIG. 7 shows that human skin fibroblasts and human skin keratinocytes with a reduced NAD content have a decreased ability to recover from exposure to solar radiation provided by a solar simulator. Restoration of normal NAD content by addition of pro-NAD agents to the culture medium of cells with a reduced NAD content resulted in restoration of a normal recovery profile. The DNA repair proficiency as a function of NAD content has been assessed also by a technique called a "comet assay." In a comet assay (O. Ostling and K. J. Johanson, Biochem. Biophys. Res. Commun. 123: 291 (1984); P. L. Olive and J. P. Banath, Exp. Cell Res. 221: 19 (1995)), cells are plated out after embedding into liquid agarose on a carrier and lysed in situ after formation of an agarose gel. The DNA of the individual cells is then separated in situ in an electric field. Damaged DNA containing strand breaks migrates away from the cell nucleus due to its smaller size and this migration results in an image where the nucleus appears as the head of the comet and the broken DNA appears as tail of the comet. The more degraded the genomic DNA is, the greater the amount of migration-capable DNA and the longer the "comet tail."

Figure 8:
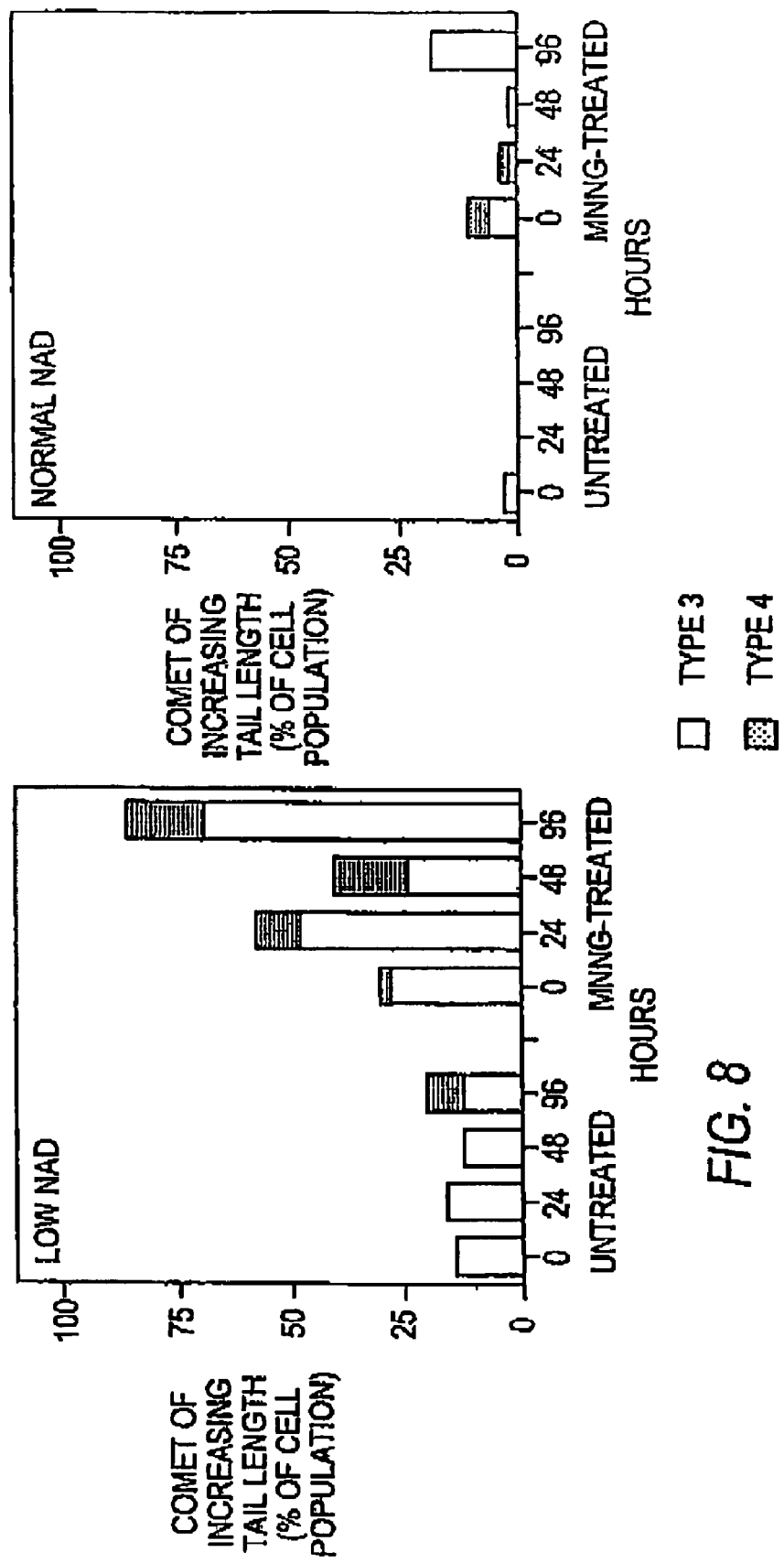
FIG. 8 depicts DNA integrity, as measured by the comet assay, of human cells as a function of NAD content both in the absence and following genotoxic stress.
Figure 10:
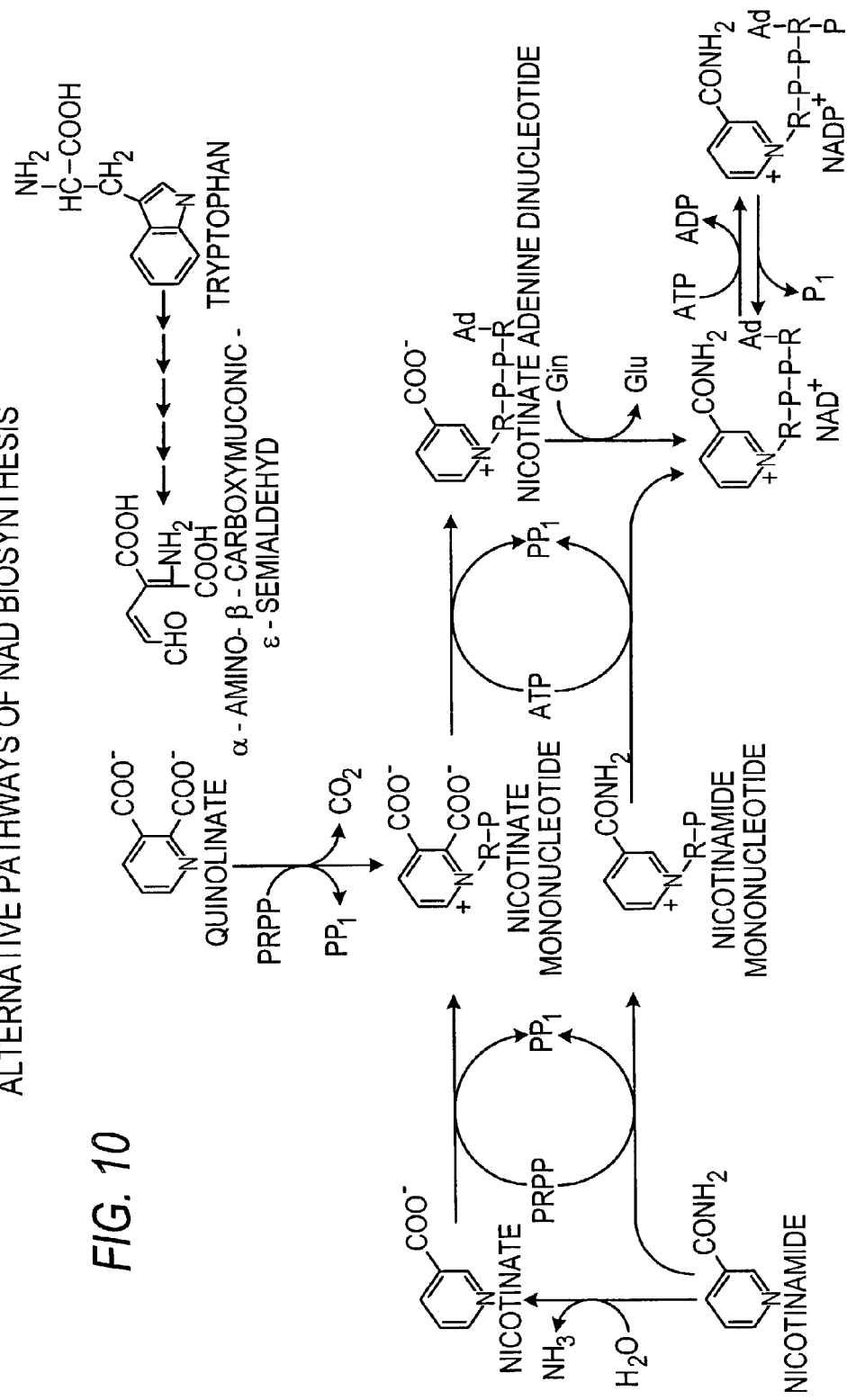
FIG. 10 depicts three possible biosynthetic pathways for the synthesis of NAD present in human cells.

FIG. 8 shows the analysis of DNA integrity of human cells as a function of NAD content both in the absence and following genotoxic stress. The results show the percentage of "type 3" and "type 4" comets which correspond to the cells with the highest levels of unrepaired damage. First, the experiment shows that cells with a sub-optimal NAD content have a significant amount of unrepaired damage even without genotoxic stress. Second, cells with low NAD show much higher levels of unrepaired damage following genotoxic stress.

EXAMPLE 4

Figure 3:
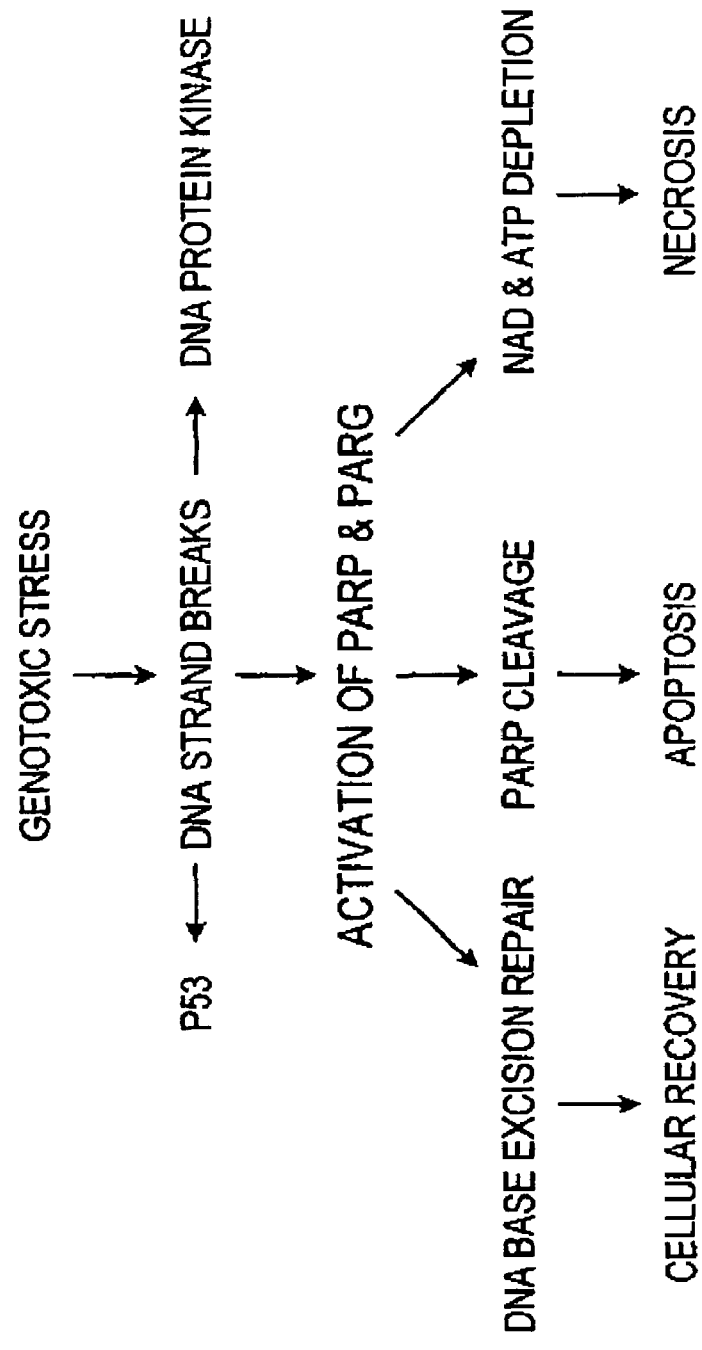
FIG. 3 depicts an overview of the involvement of PARPs and PARG in protective cellular responses to genotoxic stress.

Human Cells with a Decreased NAD Content Also Have Other Altered DNA Damage Response-Signaling Pathways As shown in FIG. 3, DNA damage signaling pathways involving NAD interact with other DNA damage signaling pathways. One of the major pathways involves the protein p53. The cellular content of p53 is normally low in the absence of genotoxic stress, but increases rapidly following the appearance of DNA strand breaks. Briefly, cells were grown in control or suboptimal niacin media as described in Example 1 above, resulting in cells with normal or low NAD content. The protein of the cells was then extracted and portions of the extract were separated by SDS-polyacrylamide gel electrophoresis (SDS-PAGE) and p53 protein content was determined by immunoblotting (western blotting). FIG. 9A shows that the cellular content of p53 in cells having normal or low NAD content as determined by immunoblotting for the p53 protein. Cells with a low NAD content have a much higher content of p53, demonstrating that a low NAD content results in an alteration of the p53 signaling pathway. FIG. 9B compares the relative content of p53 following genotoxic stress caused by the alkylating agent MNNG in cells with a low or normal NAD content. At 6 hours following DNA damage, the p53 content is elevated relative to the cells with normal NAD content, while at 24 hours following damage; the p53 content is greatly reduced relative to cells with normal NAD content.

EXAMPLE 5

Determining the Optimal Pro-NAD Agent

Two different biosynthetic pathways can elevate the NAD content of human skin cells. A series of experiments were performed to determine the possible classes of pro-NAD agents that may be used for the elevation of skin cell NAD content by topical application. Any compound that can be converted to NAD is referred to here as a "pro-NAD" agent. The pathway for the conversion of tryptophan to NAD functions only in liver and thus the remaining two pathways were evaluated in human skin cells. One of these pathways involves the conversion of nicotinamide to nicotinamide mononucleotide and then to NAD by the action of nicotinamide phosphoribosyltransferase and nicotinamide mononucleotide adenyltransferase, respectively. The second pathway involves the conversion of nicotinic acid to nicotinic acid mononucleotide with subsequent conversion to nicotinic acid adenine dinucleotide and NAD by the action of nicotinic acid phosphoribosyltransferase, nicotinic acid mononucleotide adenyltransferase, and NAD synthase, respectively.

Figure 11:
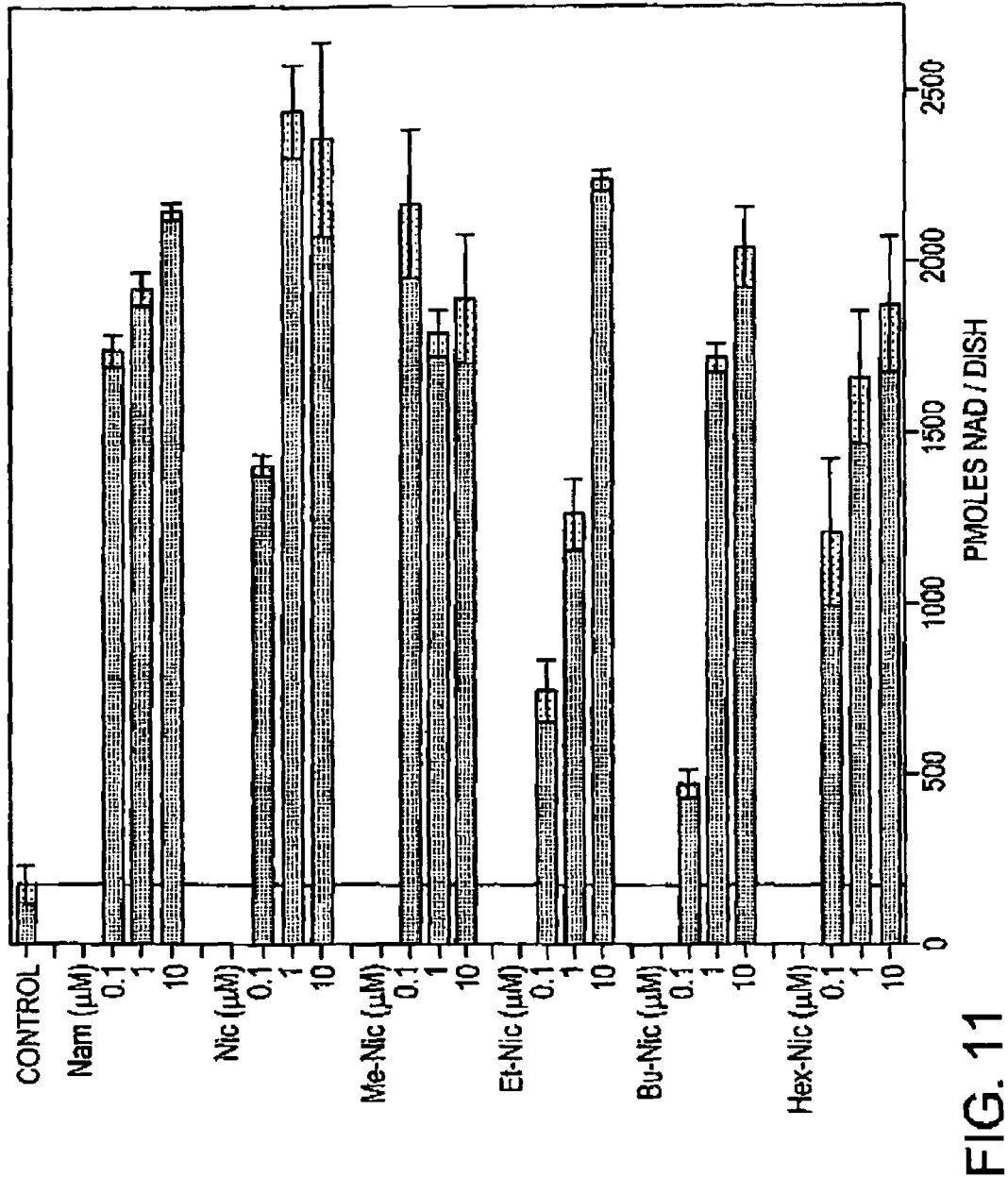
FIG. 11 depicts experimental results which show that nicotinamide, nicotinic acid, and 4 different esters of nicotinic acid can be bioconverted to NAD by skin fibroblasts.

Based on the above mentioned model, we have grouped pro-NAD agents into four classes: (1) nicotinamide, (2) any derivative of nicotinamide that can be chemically or enzymatically converted to nicotinamide, (3) nicotinic acid, and (4) any derivative of nicotinic acid that can be chemically or enzymatically converted to nicotinic acid. Experiments have been conducted with three of the four classes described above using human skin fibroblasts in culture and the results of a typical experiment are shown in FIG. 11. The results demonstrate that nicotinamide, nicotinic acid, and four different esters of nicotinic acid can be bioconverted to NAD by skin fibroblasts. Derivatives of nicotinamide that can be bioconverted to nicotinamide are expected to serve as pro-NAD agents based on the results disclosed here for nicotinamide.

EXAMPLE 6

Figure 12A:
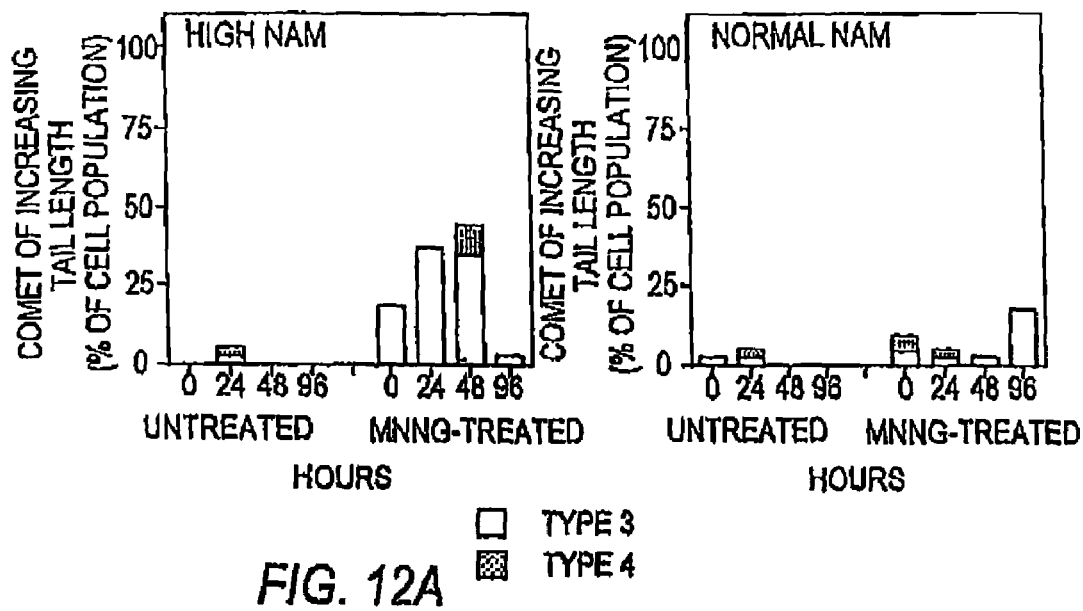
FIG. 12 Panel A compares DNA integrity in cells cultured in normal levels (50 micromolar) or high levels (500 micromolar) of nicotinamide following genotoxic stress. Panel B depicts the effects of high levels of nicotinamide or high levels of nicotinic acid on the p53-signaling pathway.
Figure 12B:
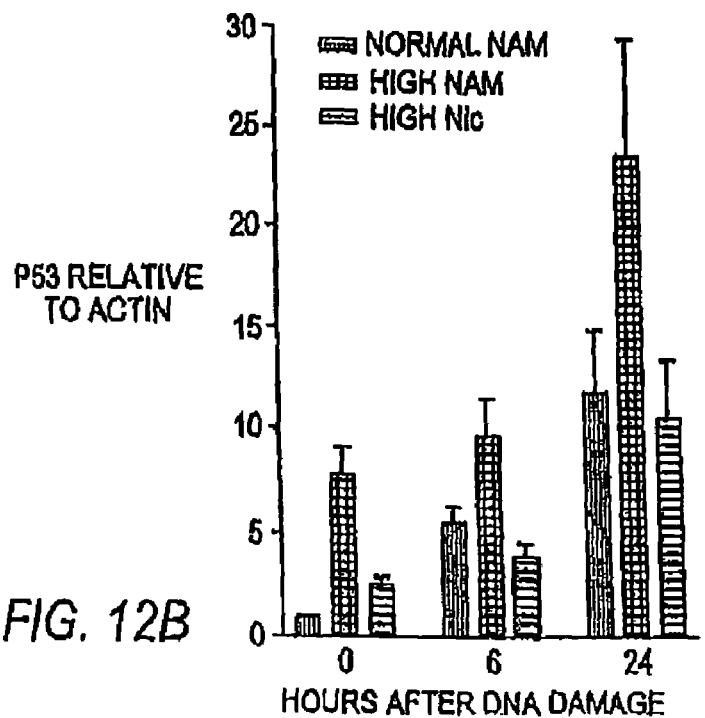

The Nicotinic Acid Pathway is Preferred for Elevation of Skin Cell NAD Content The experiments of the previous section demonstrated that two different biosynthetic pathways can elevate skin cell NAD content. In considering the relative merit of the two pathways, a tentative conclusion was reached that the nicotinic acid pathway may be a preferred pathway. While not wishing to be bound by any theory, our reasoning appears below. This conclusion was based on the realization that nicotinamide at high levels can inhibit DNA repair because it is an inhibitor of cellular PARPs, while nicotinic acid does not affect the activity of PARPs. The conclusion that elevation of NAD by the nicotinic acid pathway was preferred was confirmed by experiments, which examined the effects of high levels of nicotinic acid or nicotinamide (Nam) on DNA repair, and other DNA damage signaling pathways. FIG. 12A compares DNA integrity in cells cultured in normal levels (50 micromolar) or high levels (500 micromolar) of nicotinamide following genotoxic stress induced by the alkylating agent MNNG. It can be seen that the presence of high nicotinamide results in decreased DNA integrity as a result of inhibition of DNA repair and DNA damage response pathways. The effects of high levels of nicotinamide or high levels of nicotinic acid on the p53-signaling pathway are shown in FIG. 12B. The presence of high levels of nicotinamide demonstrated abnormally high levels of p53 both in the absence of and following genotoxic stress while the response in the presence of high levels of nicotinic acid was surprisingly similar to the response seen in normal levels of nicotinamide. These experiments show that the nicotinic acid pathway is a preferred pathway for elevation of NAD content of skin cells.

EXAMPLE 7

Topical Delivery is a Preferred Route for Elevation of Skin Cell NAD Content The discovery that the nicotinic acid pathway is a preferred pathway for elevation of skin cell NAD content lead to a series of experiments to determine if the topical route of delivery rather than a systemic delivery route is a preferred route of delivery of pro-NAD nutrients to skin cells. Skin is at the distal end of the systemic delivery system, oral intake of pro-NAD nutrients is subject to first pass liver metabolism, and the uppermost layers of the skin are poorly vascularized. Each of these factors indicates that very large oral doses of pro-nutrients would be required to provide efficient systemic delivery of pro-NAD agents to skin cells.

Experiments were conducted to determine a preferred method for the elevation of skin cell NAD content by topical delivery. One goal of the experiment was to develop methods of sustained delivery of nicotinate to skin cells with minimal (and preferably none) systemic delivery. Towards that end, the design of one preferred pro-NAD agent had the following criteria (1) the pro-NAD agent must be sufficiently lipophilic to effectively partition into and through the stratum corneum; (2) the pro-NAD agent must be slowly converted to nicotinate by skin esterases so that nicotinate will be effectively converted to NAD by keratinocytes and fibroblasts.

Figure 13:
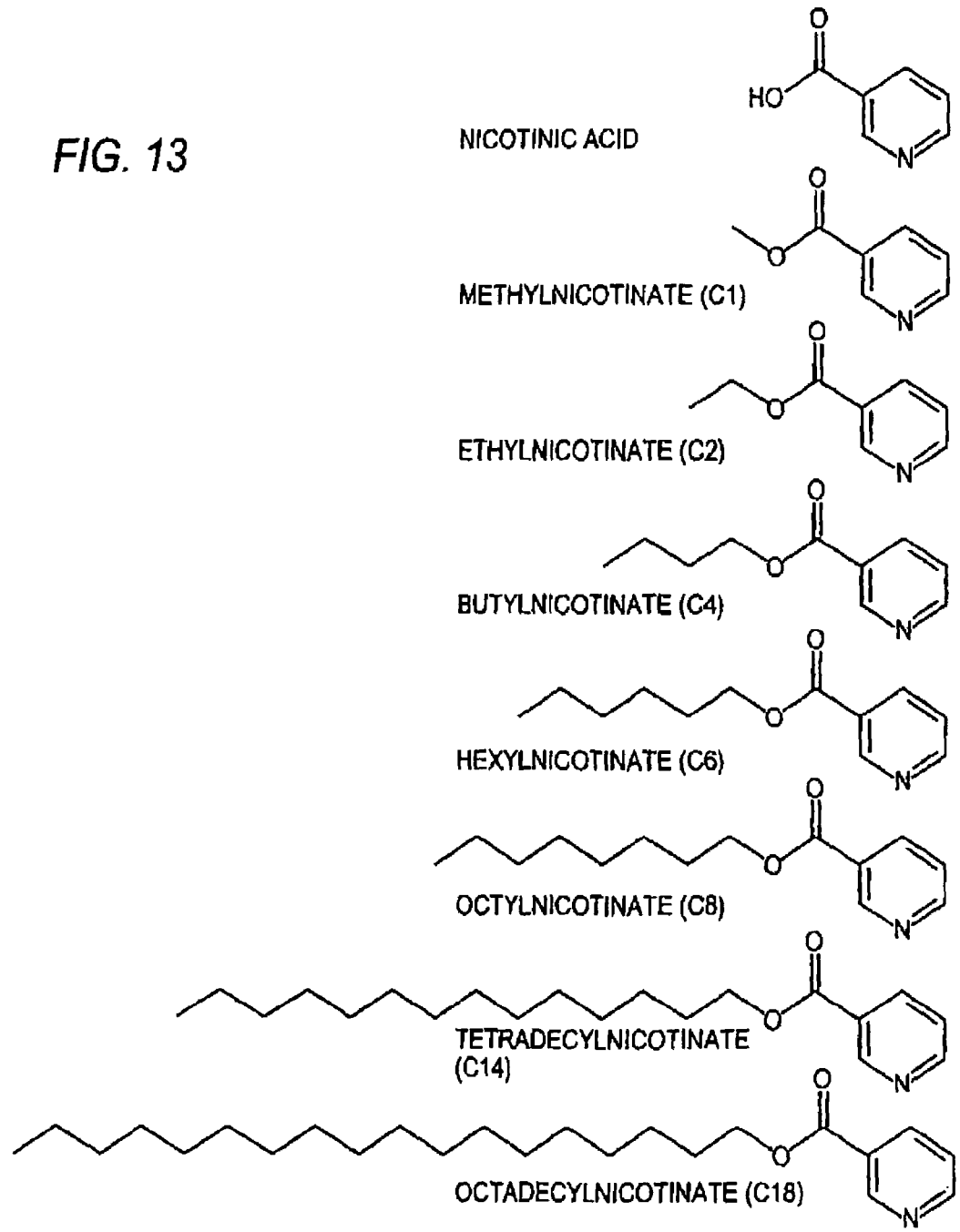
FIG. 13 depicts a series of pro-NAD agents.

The first issue considered was the physical-chemical properties of the pro-NAD agents most desirable for topical application. The nicotinic acid molecule may not be optimal because it may be too polar to be effectively delivered to skin cells topically. Molecules that are too polar may not effectively partition into the apolar stratum corneum layer of skin and following passage across the stratum corneum, it would be expected to rapidly enter the systemic circulation. A series of pro-NAD agents shown in FIG. 13 were characterized. To evaluate the potential of these pro-NAD agents to partition into the stratum corneum, the octanol/water partition coefficients for the methyl, eythl-, butyl-, hexyl-, and octyl- esters of nicotinate were experimentally determined.

Figure 14:
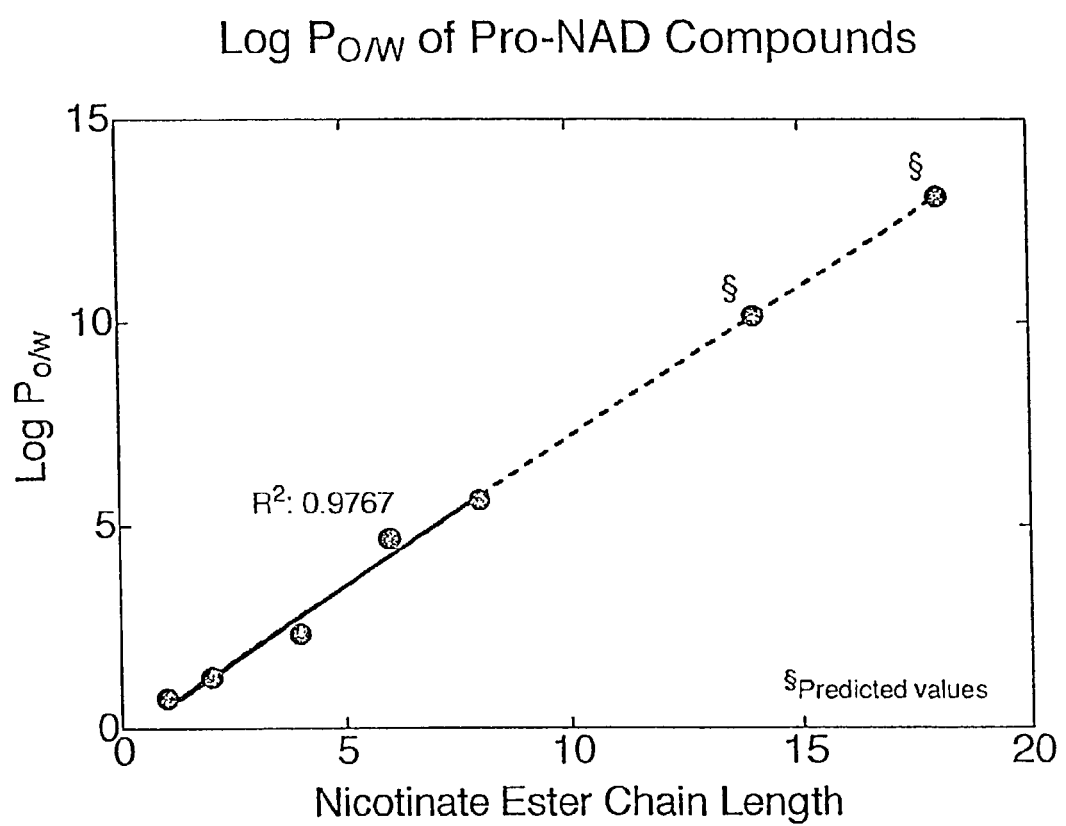
FIG. 14 depicts a plot of log $P_{o/w}$ values versus ester chain length for a series of pro-NAD agents.

The octanol/water partition coefficient was determined by dissolving a known amount of pro-NAD agent in water and then mixing the aqueous compound with a known volume of octanol. After mixing for a period of 1 to 18 hours, aliquots of the water phase were analyzed by HPLC for the amount of remaining pro-NAD agent. The partition coefficient (P) was calculated from the following equation:

$$P_{o/w} = (C_o - C)V_w/CV_o$$

$$\log P_{o/w} = \log_{10}((C_o - C)V_w/CV_o))$$

where $C_o$ is the initial concentration in water and $C$ is the concentration after partitioning. $V_w$ and $V_o$ represent the volume of water and octanol phases respectively. FIG. 14 shows a plot of log $P_{o/w}$ values versus ester chain length. FIG. 14 also shows that $P_{o/w}$ values for the tetradecyl- and octadecyl-esters of nicotinic acid maybe predicted by extrapolation of the results obtained from the experimental determination of the $P_{o/w}$ values for the shorter esters. The tetradecyl- and octadecyl-esters of nicotinate have favorable properties for partitioning into the stratum corneum and these experiments show that pro-NAD agents with log $P_{o/w}$ values in the range of 10 to 15 are optimal for effective partitioning into the stratum corneum layer of skin.

The next issue considered was the rate of hydrolysis of topically applied pro-NAD agents to nicotinic acid such that conversion to NAD can be completed by the pathway shown in FIG. 11. The rates of hydrolysis of a pro-NAD agent following topical application can be assessed by evaluation of local vasodilation following topical application of a pro-NAD agent. Nicotinate esters do not cause vasodilation and thus rates of hydrolysis that result in tissue levels of nicotinate that exceed the threshold for vasodilation can be detected following topical application. Experiments have compared the absence or presence of vasodilation (and the time course of vasodilation when present) for a number of the pro-NAD agents shown in FIG. 13. For example, application of a cream containing 0.05% hexylnicotinate results in vasodilation with onset at approximately 10 minutes and duration of approximately 90 minutes. A similar application of octylnicotinate results in an onset of vasodilation at approximately 15 minutes with duration of 360 minutes. A similar application of tetradecylnicotinate does not result in vasodilation. These experiments indicate that tetradecylnicotinate is released very slowly following application. Two factors are likely involved in the rate of hydrolysis of topically applied pro-NAD agents, the rate of departure from the stratum corneum and the rate of hydrolysis by esterases present in the epidermal and dermal layers of the skin. These experiments indicated that the longer chain esters of nicotinic acid are a preferred method for elevation of skin cell NAD content.

EXAMPLE 8

The NAD Content of Skin can be Elevated by Topical Application of Pro-NAD Agents Based on evaluation of pro-NAD agents, proof of principle experiments for elevation of skin cell NAD content by topical delivery were performed using a hairless mouse model. In brief, tetradecylnicotinate was used for the initial studies. In the study three daily topical applications of 1% tetradecylnicotinate cream to the back of the animals and no cream was applied to the abdomen. Immediately following the third application, the skin from the back and abdomen were analyzed for NAD content. Test samples of skin were frozen in liquid nitrogen and powdered by mechanical means. NAD content was assessed as described previously (Jacobson, E L, and Jacobson, M K *Meth Enzymol* 280, 221-230, 1997; Jacobson, E L et al., *J Cell Physiol* 99, 417-426, 1979). The NAD assay is based on the principle of enzymic cycling between oxidized and reduced states, in which NAD is rate-limiting for a series of amplification reactions. Total protein was assayed by the Bradford assay. The results, shown in FIG.

Figure 15:
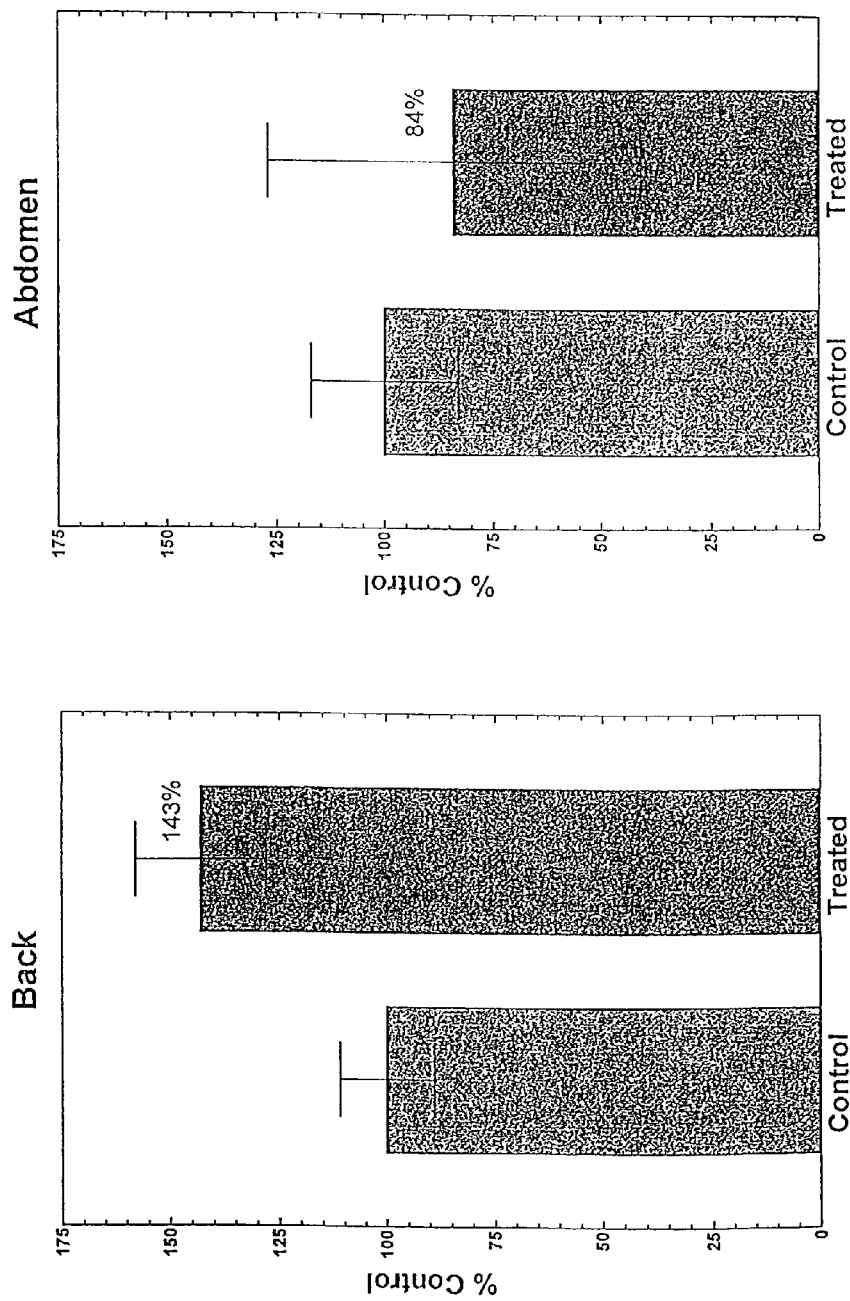
FIG. 15 depicts the results of experimental studies performed to elevate NAD levels in mouse skin by topical application of a pro-NAD agent.

15, show that three daily topical applications of a cream containing 1% tetradecylnicotinate to the back of the test animal resulted in a skin NAD content that was 143% that of a control animal treated with base cream only. FIG. 15 also show that the NAD content of skin removed from the abdomen of the treated animal was not increased, providing proof that the increased NAD content was due to topical delivery.

Figure 16:
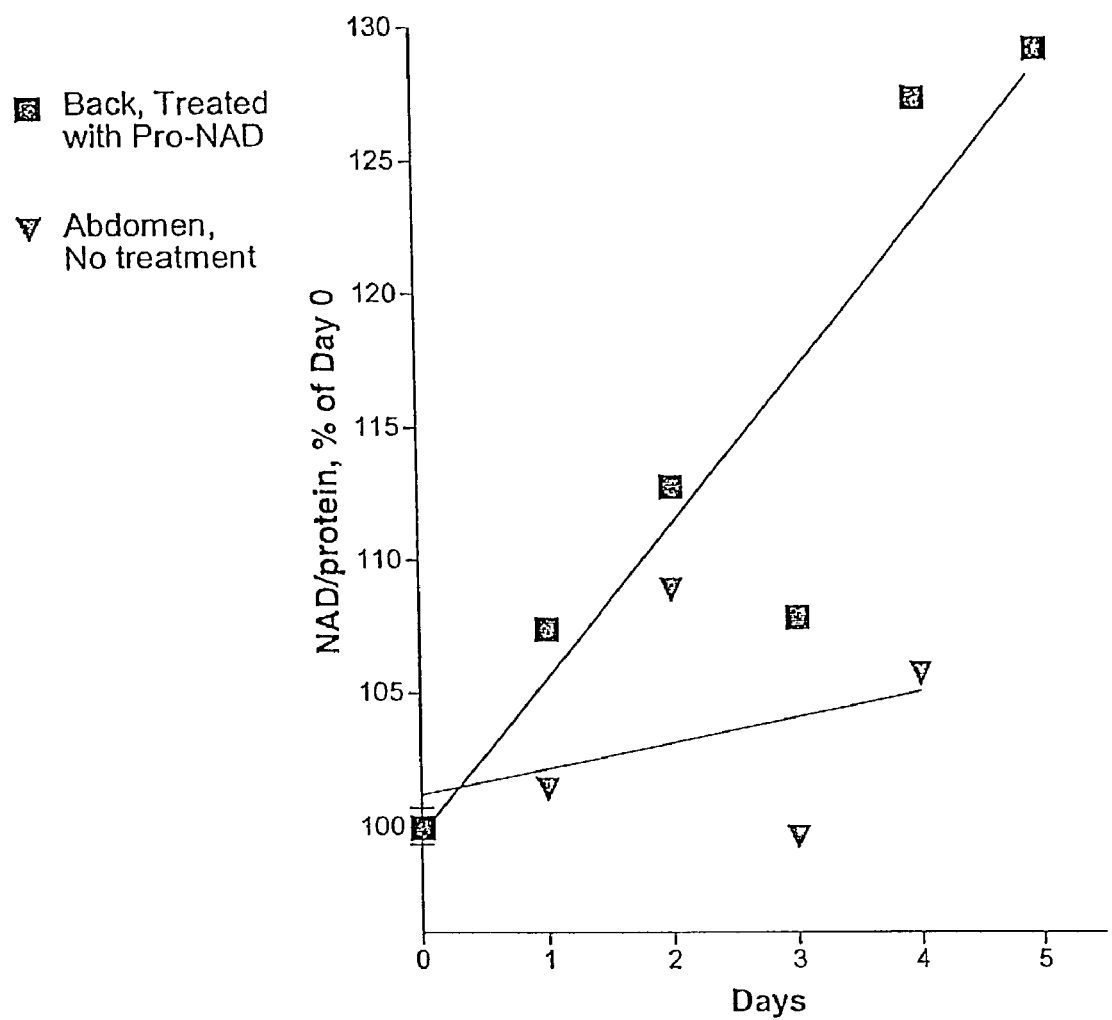
FIG. 16 depicts the results of experimental studies showing the elevation of the NAD content of mouse skin as a function of the number of daily applications of a pro-NAD agent.

In another experiment, the effect of the number of daily application of 1% tetradecylnicotinate cream was examined. Again, application was made to the back of the animal and the abdomen of each animal served as control. The results, depicted in FIG. 16, show that the NAD content of skin removed from the back increased as a function of the number of daily applications. In contrast, the NAD content of the abdomen did not increase, providing additional evidence that the increased NAD content was due to topical delivery of the pro-NAD agent.

It should be noted that in no case were any signs of toxicity observed as a result of the topical application of tetradecylnicotinate cream in the experiments shown in FIGS. 15 and 16.

Other pro-NAD agents may be identified by exposing cells in culture to candidate pro-NAD agents or by exposing skin on a test subject, such as a mouse, to the candidate pro-NAD agent. After a safe and effective dosage is determined, the candidate pro-NAD agents may be tested on human volunteers and assayed by skin biopsy samples. The effectiveness of the pro-NAD agents maybe determined by (a) biochemically analyzing cell lysates to assess the cellular NAD content or (b) scoring phenotypic or functional changes in treated cells as compared to control cells that were not exposed to the candidate pro-NAD agent.

Where analogs and derivatives of a known pro-NAD agent are to be identified or evaluated, the cells are exposed to the pro-NAD agent of the invention and compared to positive controls which are exposed only to the known pro-NAD agent, and to negative controls which were not exposed to either the candidate pro-NAD agent or the known pro-NAD compound.

In order to determine if the pro-NAD agent administered according to the method of the invention is absorbed into body tissues, and if so, in which tissue absorption occurs, the following may be performed. Samples of various body tissues from a subject, such as a laboratory mouse, were analyzed for NAD content at increasing hours after oral administration of a pro-NAD agent. The results of the measurement are compared to that of control subjects to determine the percent increase of NAD content. A dose response curve and a therapeutic index can be developed to determine the optimal oral dosage.

Other embodiments and uses of the invention will be apparent to those skilled in the art from consideration of the specification and practice of the invention disclosed herein. All U.S. patents and applications and other references noted herein are specifically incorporated by reference. The specification and examples should be considered exemplary only with the true scope and spirit of the invention indicated by the following claims.

What is claimed is:

1. A composition for increasing intracellular NAD content, comprising a hexadecyl nicotinic acid ester, tocopheryl acetate and a pharmaceutically acceptable carrier.

2. The composition of claim 1, wherein said hexadecyl nicotinic acid ester is presented in said composition at from about 0.001% to about 10% by weight of said composition.

3. The composition of claim 2, wherein said hexadecyl nicotinic acid ester is present in said composition at from about 0.01% to about 3% by weight of said composition.

4. The composition of claim 3, wherein said hexadecyl nicotinic acid ester is present in said composition at about 1% by weight of said composition.

5. A composition for increasing intracellular NAD content comprising:
   (i) a hexadecyl nicotinic acid ester;
   (ii) an antioxidant, a sun screen, a vitamin or a pH stabilizer;
   (iii) tocopheryl acetate, and
   (iv) a pharmaceutically acceptable carrier.

6. The composition of claim 5, wherein (ii) is an antioxidant.

7. The composition of claim 5, wherein (ii) is a sun screen.

8. The composition of claim 5, wherein (ii) is a vitamin.

9. The composition of claim 5, wherein (ii) is a pH stabilizer.

10. The composition of claim 5, wherein (i) is present at from about 0.001% to about 10% by weight of said composition.

11. The composition of claim 10, wherein (i) is present at from about 0.01% to about 3% by weight of said composition.

12. The composition of claim 11, wherein (i) is present at about 1% by weight of said composition.

* * * * *